(12) United States Patent
Van Zon et al.

(10) Patent No.: US 10,876,964 B2
(45) Date of Patent: *Dec. 29, 2020

(54) SYSTEM, APPARATUS AND METHOD FOR DETERMINING A SUBSTANCE WITHIN A FLUID

(75) Inventors: Joannes Baptist Adrianus Dionisius Van Zon, Waalre (NL); Toon Hendrik Evers, Eindhoven (NL); Maatje Koets, Wageningen (NL)

(73) Assignee: Koninklijke Philips N.V., Eindhoven (NL)

(*) Notice: Subject to any disclaimer, the term of this patent is extended or adjusted under 35 U.S.C. 154(b) by 515 days.

This patent is subject to a terminal disclaimer.

(21) Appl. No.: 13/515,853

(22) PCT Filed: Dec. 10, 2010

(86) PCT No.: PCT/IB2010/055722
§ 371 (c)(1),
(2), (4) Date: Jun. 20, 2012

(87) PCT Pub. No.: WO2011/073866
PCT Pub. Date: Jun. 23, 2011

(65) Prior Publication Data
US 2012/0252033 A1    Oct. 4, 2012

(30) Foreign Application Priority Data

Dec. 18, 2009 (EP) .................................. 09179977

(51) Int. Cl.
*G01N 33/543* (2006.01)
*G01N 21/552* (2014.01)

(52) U.S. Cl.
CPC ..... *G01N 21/552* (2013.01); *G01N 33/54373* (2013.01)

(58) Field of Classification Search
CPC ................................................ G01N 33/54333
See application file for complete search history.

(56) References Cited

U.S. PATENT DOCUMENTS 5,658,723 A * 8/1997 Oberhardt ..................... 435/4
5,719,063 A * 2/1998 Block ........................ 436/501
(Continued)

FOREIGN PATENT DOCUMENTS

WO    199936577 A1    7/1999
WO   2006134546 A2   12/2006
(Continued)

OTHER PUBLICATIONS

Pamme, N., "Magnetism and Microfluidics" Lab on a Chip (2006) 6:24-38.*
(Continued)

*Primary Examiner* — Rebecca M Giere

(57) ABSTRACT

The invention relates to a substance determining apparatus and method for determining a substance within a fluid. Particles attach to the substance and bind to a binding surface (30), wherein a particle release curve being indicative of a release of bound particles from the binding surface (30) is determined, and a part of the particle release curve caused by particles bound to the binding surface via a predefined kind of binding is determined based on the temporal behaviour of the particle release curve. The substance within the fluid is determined based on the part of the particle release curve. The substance can therefore be determined based on particles which are bound to the binding surface via a certain kind of binding, i.e. other kinds of binding substantially do not affect the determination of the substance, thereby improving the accuracy of determining the substance.

13 Claims, 8 Drawing Sheets

(56) References Cited

U.S. PATENT DOCUMENTS

| | | | |
|---|---|---|---|
| 6,592,822 B1 * | 7/2003 | Chandler | 422/82.05 |
| 8,697,435 B2 * | 4/2014 | Heil et al. | 435/288.7 |
| 8,822,227 B2 * | 9/2014 | Kahlman | 436/164 |
| 9,410,948 B2 * | 8/2016 | Dittmer | G01N 33/54326 |
| 2006/0024756 A1 * | 2/2006 | Tibbe et al. | 435/7.2 |
| 2007/0231796 A1 | 10/2007 | Majda | |
| 2010/0194386 A1 * | 8/2010 | Prins et al. | 324/228 |
| 2010/0248973 A1 * | 9/2010 | Van Lankvelt et al. | 506/7 |
| 2010/0273269 A1 * | 10/2010 | Van Lankvelt et al. | 436/149 |
| 2011/0012596 A1 * | 1/2011 | Menon et al. | 324/309 |
| 2011/0279114 A1 * | 11/2011 | Van Zon et al. | 324/244.1 |
| 2012/0258553 A1 * | 10/2012 | Dittmer et al. | 436/501 |
| 2015/0024376 A1 * | 1/2015 | Ozanich | 435/5 |
| 2016/0291004 A1 * | 10/2016 | Sijbers | B03C 1/282 |

FOREIGN PATENT DOCUMENTS

| | | | | | |
|---|---|---|---|---|---|
| WO | 2006138294 A2 | 12/2006 | | | |
| WO | WO 2009/013662 A1 * | 1/2009 | | | G01N 33/543 |
| WO | 2009037636 A1 | 3/2009 | | | |
| WO | 2009063391 A1 | 5/2009 | | | |
| WO | WO 2009/072045 A1 * | 6/2009 | | | G01N 33/543 |
| WO | 2009083814 A2 | 7/2009 | | | |
| WO | 2009093160 A1 | 7/2009 | | | |
| WO | 2009098623 A1 | 8/2009 | | | |
| WO | 2009125356 A1 | 10/2009 | | | |

OTHER PUBLICATIONS

Hahnefeld et al. "Determination of Kinetic Data Using Surface Plasmon Resonance Biosensors", From: Methods in Molecular Medicine, vol. 94: Molecular Diagnosis of Infectious Diseases, 2/e; Edited by: J. Decker and U. Reischl © Humana Press Inc., Totowa, NJ.*

* cited by examiner

SYSTEM, APPARATUS AND METHOD FOR DETERMINING A SUBSTANCE WITHIN A FLUID

FIELD OF THE INVENTION

The invention relates to a substance determining apparatus and substance determining method for determining a substance within a fluid. The invention relates further to a binding device and an analyzing device for cooperating with each other for determining a substance within a fluid, to an analyzing method for determining a substance within a fluid, and an analyzing computer program for determining a substance within a fluid.

BACKGROUND OF THE INVENTION

WO 2009/098623 A1 discloses a magnetic biosensor based on magnetic beads that can be actuated with electromagnetic fields. The magnetic beads are functionalized with antibodies that can bind a specific analyte molecule in a sample. The beads are attracted to the sensor surface, where the number of bound beads is directly or inversely related to the amount of analyte molecules present in the sample. The beads are then detected by a technique which is based on frustrated total internal reflection (FTIR).

SUMMARY OF THE INVENTION

It is an object of the present invention to provide a substance determining apparatus and substance determining method for determining a substance within a fluid, which allows increasing the accuracy of determining the substance. It is a further object of the present invention to provide a corresponding binding device and analyzing device for cooperating with each other for determining a substance within a fluid, an analyzing method for determining a substance within a fluid, and an analyzing computer program for determining a substance in a fluid.

In a first aspect of the present invention a substance determining apparatus for determining a substance within a fluid is presented, wherein the substance determining apparatus comprises:
  particles for being attached to the substance within the fluid,
  a binding surface for binding the particles, if the particles have been attached to the substance, wherein the particles are bindable to the binding surface with different kinds of binding,
  a sensing unit for sensing the particles on the binding surface, wherein the sensing unit is adapted to generate a temporal sensing signal depending on the bound particles,
  a particle release curve determination unit for determining a particle release curve being indicative of a release of bound particles from the binding surface depending on the generated temporal sensing signal,
  a binding determination unit for determining a part of the particle release curve caused by particles bound to the binding surface via a predefined kind of binding based on a temporal behaviour of the particle release curve,
  a substance determination unit for determining the substance within the fluid based on the determined part of the particle release curve.

It has been found that the temporal behaviour of the particle release curve is indicative of the kinds of binding between the particles and the binding surface. Thus, by determining a part of the particle release curve caused by particles bound to the binding surface via a predefined kind of binding based on the temporal behaviour and by determining the substance within the fluid based on the determined part of the particle release curve, the substance can be determined based on particles which are bound to the binding surface via a certain kind of binding, i.e. other kinds of binding substantially do not affect the determination of the substance, thereby improving the accuracy of determining the substance.

The substance determining apparatus is preferentially a magnetic biosensor, wherein the particles are magnetic beads, i.e. nanoparticles, which label the substance. The magnetic beads are preferentially functionalized with an attaching element that can be attached to the substance being, for example, a specific analyte molecule. The attaching element is, for example, an antibody, a protein, DNA, an aptamer et cetera. The substance determination apparatus is preferentially adapted to perform a sandwich immunoassay.

The sensing unit preferentially comprises a light source for generating radiation for being directed to the binding surface for generating an evanescent field and a light detector for detecting light from the binding surface, wherein the detected light has been influenced by the particles bound on the binding surface by influencing the evanescent field and wherein the sensing signal is generated depending on the detected influenced light.

Preferentially, the light from the light source is directed to binding surface such that it is totally internally reflected for generating the evanescent field. The totally internally reflected light is detected by the light detector, wherein the detected light is influenced by absorption and scattering of the evanescent light by the particles bound on the binding surface. As a result the light intensity detected by the light detector is modified. The generated sensing signal is preferentially indicative of this change in light intensity caused by absorption and scattering of the evanescent light by the particles bound on the binding surface.

The light source preferentially comprises a light emitting diode or a laser for exciting the evanescent field.

The particle release curve is preferentially regarded as being a superposition of sub particle release curves, wherein at least one of the sub particle release curves is caused by particles bound to the binding surface via the predefined kind of binding. This at least one sub particle release curve can be regarded as the part of the particle release curve determined by the binding determination unit caused by particles bound to the binding surface via the predefined kind of binding. The sub particle release curves are preferentially exponentially decaying curves, wherein the binding determination unit is preferentially adapted to fit the superposition of these exponentially decaying curves to the determined particle release curve for determining a part of the particle release curve caused by particles bound to the binding surface via the predefined kind of binding.

In an embodiment, the sensing unit is adapted to generate a temporal sensing signal dependent on the bound particles integrated over a predefined region of the binding surface, wherein the particle release curve determination unit is adapted to determine the generated temporal sensing signal as the particle release curve. This allows to determine the particle release curve in a simple way by using the generated temporal sensing signal. The temporal sensing signal is preferentially a FTIR sensing signal.

The particle release curve determination unit can also be adapted to
determine lifetimes of the bindings of the particles on the binding surface from the generated sensing signal,
generate a histogram of the determined lifetimes, and
determine the particle release curve depending on the generated histogram. Preferentially, the sensing unit is adapted such that the generated sensing signal is indicative of starting moments and ending moments of single binding events, wherein the particle release curve determination unit is adapted to determine the lifetimes of the bindings, i.e. the lifetimes of the binding events, by determining the starting moments and the ending moments of the single binding events from the generated sensing signal. The sensing unit can be adapted to generate images of the binding surface at different times as the sensing signal, wherein an image shows at which positions on the binding surface particles are bound at a time and wherein the particle release curve determination unit is adapted to determine the starting moments and the ending moments by comparing temporally consecutive images. The images are preferentially generated from evanescent light scattered by the particles bound on the binding surface based on dark field microscopy.

The sensing unit preferentially comprises a force applying unit for applying a force to the particles for putting bindings between the particles and the binding surface under stress, while sensing the particles.

By applying a force to the particles for putting bindings between the particles and the binding surface under stress, while sensing the particles, the temporal behaviour of the particle release curve can be modified such that a part of the particle release curve caused by particles bound to the binding surface via a predefined kind of binding can be determined with an improved quality. For example, the temporal behaviour can be defined by several time constants corresponding to different kinds of binding, for example, corresponding to a specific kind of binding and a non-specific kind of binding. Preferentially, the force is applied to the particles such that these time constants can be determined and separated from each other more reliably, thereby further improving the sensitivity of the substance determining apparatus. Preferred forces can be determined by calibration, wherein time constants are determined and separated from each other for different forces and a force is determined, which allows determining and separating time constants with the largest reliability.

The force applying unit is preferentially a magnetic unit for applying magnetic forces to the particles bound to the binding surface. The particles are preferentially particles which can be forced by a magnetic field. The magnetic unit can be adapted such that the particles can be attracted towards the binding surface or pulled away from the binding surface. The magnetic unit can also be adapted to modify the in-plane position of the bound particles, i.e. to move the particles in a lateral direction parallel to the binding surface. Moreover, the magnetic unit can be adapted such that the orientation of the particles, which are preferentially magnetic particles, can be modified.

In addition to or in an alternative, the force applying unit can be adapted to apply another force to the particles for putting the bindings between the particles and the binding surface under stress. For example, the force applying unit can be adapted to apply fluidic, electrostatic, sonic, et cetera, forces to the particles bound to the binding surface. In particular, an ionic content of the fluid can be modified for modifying the distance of the particles bound to the binding surface and the binding surface, thereby modifying the stress applied to the bindings.

The substance determining apparatus is preferentially adapted to provide a binding phase and a washing phase. In the binding phase the force applying unit forces the particles towards the binding surface, in order to allow the particles to be bound to the binding surface, and preferentially the unbound particles away from the binding surface in an alternating way, i.e. in the binding phase preferentially the force applying unit forces the particles alternately towards the binding surface and away from the binding surface. In the binding phase, particles can be bound to the binding surface and bindings can be broken. In the following washing phase the force applying unit applies a force to the particles, which urges the particles only away from the binding surface, thereby washing unbound particles away from the binding surface and putting the bindings between bound particles and the binding surface under stress. In the washing phase preferentially new bindings are not generated and also bound particles are released from the binding surface. The sensing unit can be adapted to generate a sensing signal being indicative of lifetimes of single binding events during the binding phase and/or during the washing phase. The particle release curve determination unit can therefore be adapted to determine the particle release curve depending on a histogram of these lifetimes determined based on the sensing signal generated in the binding phase and/or the washing phase. This can allow for determining the substance within the fluid not only in the washing phase, but also in the binding phase.

Preferentially, the sensing unit is adapted to sense the particles during a predefined sensing time, wherein the force applying unit is adapted to apply the force such that particles bound to the binding surface via the predefined kind of binding are released mainly outside the sensing time and particles bound to the binding surface via another kind of binding are released mainly inside the sensing time.

This increases the differences in the temporal behaviour of the part of the particle release curve caused by particles bound to the binding surface via the predefined kind of binding and the part of the particle release curve caused by particles bound to the binding surface via another kind of binding, thereby allowing increasing the quality of determining the part of the particle release curve caused by particles bound to the binding surface via the predefined kind of binding and, thus, improving the sensitivity of determining these particles.

It is further preferred that the binding determination unit is adapted to
provide a first predefined fitting release curve having a first temporal behaviour being indicative of a first kind of binding and a second predefined fitting release curve having a second temporal behaviour being indicative of a second kind of binding,
fit the first predefined fitting release curve and the second predefined fitting release curve to the determined particle release curve by fitting a linear combination of the first predefined fitting release curve and the second predefined fitting release curve to the determined particle release curve,
determine one of the fitted first predefined release curve and the fitted second predefined release curve as the part of the particle release curve caused by particles bound to the binding surface via a predefined kind of binding. For example, the first kind of binding can be a specific binding and the second kind of binding can be non-specific binding. The first predefined fitting release curve is preferentially determined by calibration, wherein only the first kind of binding is present, and the second predefined fitting release curve is preferentially determined by calibration, wherein only the second kind of binding is present. The first predefined fitting release curve and the second predefined fitting release curve can therefore be regarded as calibration curves, which can be real measured curves, for example, a table with measured values, or parametric curves in which the parameters are determined by fitting the parametric curve to the measured curves. A parametric curve can be any model which describes the measured data such as a polynomial, a Fourier series, a linear superposition of exponentially decaying signals, et cetera.

It is further preferred that the binding determination unit is adapted to determine time constants of the particle release curve as the temporal behaviour of the particle release curve, wherein the time constants are defined by reaction constants of the particles bound to the binding surface, and wherein the binding determination unit is adapted to determine a part of the particle release curve, which changes with at least one of the determined time constants, as the part of the particle release curve caused by particles bound to the binding surface via the predefined kind of binding.

Preferentially, a linear combination of exponential curves is fitted to the particle release curve for determining the time constants, wherein different time constants can be indicative of different kinds of binding. Thus, by determining a part of the particle release curve, which changes with at least one of the determined time constants, and by determining the substance within the fluid based on this determined part of the particle release curve, a substance can be determined which is related to the kind of binding which corresponds to the at least one of the determined time constants. The time constant preferentially relates to a specific binding of a particle of the substance to be determined.

In particular, when measuring low analyte concentrations, in the prior art the sensitivity is generally determined by a part of the sensing signal that is obtained for the low analyte concentration and a part of the sensing signal that is obtained for a blank measurement, containing no analyte. It has been observed that the part of the sensing signal for the blank measurement is not only determined by instrument noise, but also by particles binding to the surface, independent of the presence of an analyte, i.e. that an additional contribution to the sensing signal is generated by non-specific binding. Since this non-specific binding can occur, increasing the instrumental signal per particle may not increase the overall sensitivity, as the signal for the non-specific binding may also be increased. But, since according to the invention the substance determination unit can be adapted to consider only specifically bound particles, the accuracy of determining the substance within the fluid can be further improved.

Specifically bound particles are preferentially particles which have been attached to the substance and which have been bound to the binding surface. In particular, a specific binding is preferentially a binding that depends on the presence of the substance, i.e. it preferentially describes a binding, wherein a particle has been attached to the substance and is bound to the binding surface, whereas non-specific binding is preferentially a binding that is not dependent on the presence of the substance, i.e. it preferentially describes a presence of particles on the binding surface, wherein the particles have not been attached to the substance.

The substance determination unit is preferentially adapted to determine the amount or the concentration of the particles within the fluid, in particular, based on a part of the temporal sensing signal caused by specifically bound particles on the binding surface only.

It is further preferred that the sensing unit comprises a force applying unit for applying a force to the particles for putting bindings between the particles and the binding surface under stress, while sensing the particles, wherein the binding determination unit is adapted to correct the time constants for the influence of the applied force based on the applied force and to determine a part of the particle release curve, which changes with at least one of the corrected time constants, as the part of the particle release curve caused by particles bound to the binding surface via the predefined kind of binding. This allows the binding determination unit to modify the temporal behaviour of the generated sensing signal by applying a force to the particles for putting bindings between the particles and the binding surface under stress and to determine the time constants being indicative of the kinds of binding, which would have been measured, if the force would not have been applied to the particles. The force can therefore be applied such that, for example, different temporal behaviours related to different kinds of binding are more pronounced in the particle release curve, wherein the time constants defined by the reaction constants of the particles bound to the binding surface can still be assigned to certain kinds of binding by using the corrected time constants. The time constants and, thus, the corresponding reaction constants can therefore be determined with an increased accuracy, wherein the time constants, i.e. the corrected time constants, can still be assigned to the respective certain kinds of binding.

It is further preferred that the particles are magnetic particles with magnetic properties, which magnetically influence each other, thereby influencing the time constants, wherein the sensing unit is adapted to generate a temporal position signal being indicative of the positions of the particles, wherein the binding determination unit is adapted to:

determine the positions of the particles for different times from the generated temporal position signal, determine the magnetic particle-particle influence based on the determined positions and magnetic properties of the particles at the different times, correct the time constants depending on the determined magnetic particle-particle influence at the different times.

determine a part of the particle release curve, which changes with at least one of the corrected time constants, as the part of the particle release curve caused by particles bound to the binding surface via the predefined kind of binding.

Since the positions of the magnetic particles are determined from the generated position signal and since the magnetic properties, in particular, the magnetic moment, of the magnetic particles are known or can be calculated, the magnetic force between the magnetic particles can also be determined. This magnetic force, i.e. the magnetic particle-particle influence, can be used to correct the time constants, thereby improving the quality of determining the time constants, and, thus, of distinguishing between certain kinds of binding.

The sensing unit preferentially comprises a light source for generating radiation for being directed to the binding surface for generating an evanescent field and a light detector for detecting light from a detection plane being parallel to the binding surface or defined by the binding surface, wherein the detected light has been influenced by the particles in the detection plane by influencing the evanescent field, wherein the position signal is generated depending on the detected influenced light and indicative of the positions of the particles within the detection plane. In particular, the light detector is adapted to move the detection plane with respect to the binding surface for generating the position signal indicative of height positions of the particles with respect to the binding surface. This allows determining the three-dimensional position of the particles by determining the two-dimensional position within the detection plane and by knowing the distance of the detection plane to the binding surface.

Preferentially, evanescent light is scattered by the particles bound on the binding surface, and the scattered light is detected by the light detector.

The sensing unit preferentially comprises an objective lens for collecting the light of the evanescent field scattered by the bound particles on the binding surface, wherein the collected scattered light is imaged onto a two-dimensional light detector like a CCD- or CMOS-camera by an imaging unit like an imaging lens. This allows using dark field microscopy (DFM) for generating a position signal. As already mentioned above, this DFM signal can also be used as sensing signal, or the DFM signal can be used as a position signal and a FTIR signal can be used as the sensing signal.

In order to define the detection plane, the light detector preferentially comprises focusing means including, in particular, the objective lens and the imaging lens allowing to focus in the detection plane. If the focal plane, i.e. the detection plane, coincides with the binding surface, the two-dimensional position of the particles on the binding surface can be determined. By scanning the focal plane in a direction perpendicular to the binding surface, also information about the presence of particles in other planes parallel to the surface can be obtained. If, for example, the force applying unit applies a magnetic field being vertical to the binding surface, the individual length of magnetic clusters can be determined, either by counting the individual particles in a vertical chain or from height calibrated information from the focusing means.

It is further preferred that the binding determination unit is adapted to determine a part of the particle release curve caused by particles bound to the binding surface by specific bindings, wherein the substance determination unit is adapted to determine the substance within the fluid based on the determined part of particle release curve. Since the substance within the fluid is determined based on a part of the particle release curve caused by specifically bound particles and not caused by non-specifically bound particles, the accuracy of determining the substance within the fluid is further improved.

It is further preferred that
the particles comprise first particles for being attached to a first substance within the fluid and second particles for being attached to a second substance with the fluid,
the binding surface is adapted to bind the first particles, if the first particles have been attached to the first substance, and to bind the second particles, if the second particles have been attached to the second substance, wherein the first particles are bound to the binding surface with a first kind of binding and the second particles are bound to the binding surface with a second kind of binding, the sensing unit is adapted to sense the first particles and the second particles on the binding surface, wherein the sensing unit is adapted to generate a temporal sensing signal depending on the bound first and second particles, the particle release curve determination unit is adapted to determine a particle release curve being indicative of a release of the bound first and second particles from the binding surface depending on the generated temporal sensing signal, the binding determination unit is adapted to determine a first part of the particle release curve caused by first particles bound to the binding surface via the first kind of binding based on a first temporal behaviour of the particle release curve and a second part of the particle release curve caused by second particles bound to the binding surface via the second kind of binding based on a second temporal behaviour of the temporal sensing signal, the substance determination unit is adapted to determine the first substance within the fluid based on the determined first part of the particle release curve and the second substance within the fluid based on the determined second part of the particle release curve.

This allows distinguishing between the first substance and the second substance, in particular, determining the first substance within the fluid and the second substance within the fluid, by separating the temporal behaviour of the particle release curve caused by the first kind of binding from the temporal behaviour of the particle release curve caused by the second kind of binding, wherein the first kind of binding belongs to the first particles for attaching the first substance and the second kind of binding belongs to the second particles for attaching the second substance. The substance determining apparatus can therefore be adapted to distinguish between bound particles having attached the first substance and bound particles having attached the second substance, even if the corresponding binding sites are very close to each other.

The substance determination apparatus preferentially comprises a binding device, in particular, a cartridge, including the particles and the binding surface and being adapted to receive the fluid, and an analyzing device, which can be regarded as a reader, including the sensing unit, the binding determination unit and the substance determination unit.

The binding device is preferentially a disposable device and the analyzing device is preferentially a reusable device. Thus, by distributing the functionalities over the binding device and the analyzing device, a part of the substance determination apparatus can be used as a disposable device and the other part can be used as a reusable device. Since the fluid, which is preferentially a sample of a bodily fluid like blood, saliva or urine, is introduced into the binding device and since the binding device is a disposable device, the binding device can be used only one time before being disposed, i.e. a determination of the substance within the fluid is not affected by impurities of a previous measurement.

In an aspect of the present invention a binding device for cooperating with an analyzing device for determining a substance within a fluid is presented, wherein the binding device comprises
particles for being attached to the substance within the fluid, a binding surface for binding the particles, if the particles have been attached to the substance, wherein the particles are bindable to the binding surface with different kinds of binding, the analyzing device comprising:

a sensing unit for sensing the particles on the binding surface, wherein the sensing unit is adapted to generate a temporal sensing signal depending on the bound particles, a particle release curve determination unit for determining a particle release curve being indicative of a release of bound particles from the binding surface depending on the generated temporal sensing signal, a binding determination unit for determining a part of the particle release curve caused by particles bound to the binding surface via a predefined kind of binding based on a temporal behaviour of the particle release curve, a substance determination unit for determining the substance within the fluid based on the determined part of the particle release curve.

In a further aspect of the present invention an analyzing device for cooperating with a binding device for determining a substance within a fluid is presented, wherein the binding device comprises:

particles for being attached to the substance within the fluid, a binding surface for binding the particles, if the particles have been attached to the substance, wherein the particles are bindable to the binding surface with different kinds of binding, the analyzing device comprising:

a sensing unit for sensing the particles on the binding surface, wherein the sensing unit is adapted to generate a temporal sensing signal depending on the bound particles, a particle release curve determination unit for determining a particle release curve being indicative of a release of bound particles from the binding surface depending on the generated temporal sensing signal, a binding determination unit for determining a part of the particle release curve caused by particles bound to the binding surface via a predefined kind of binding based on a temporal behaviour of the particle release curve, a substance determination unit for determining the substance within the fluid based on the determined part of the particle release curve.

In a further aspect of the present invention a substance determining method for determining a substance within a fluid is presented, wherein the substance determining method comprises:

attaching particles to the substance within the fluid, binding the particles to a binding surface, if the particles have been attached to the substance, wherein the particles are bound to the binding surface with different kinds of binding, sensing the particles on the binding surface, wherein a temporal sensing signal is generated depending on the bound particles, determining a particle release curve being indicative of a release of bound particles from the binding surface depending on the generated temporal sensing signal, determining a part of the particle release curve caused by particles bound to the binding surface via a predefined kind of binding based on a temporal behaviour of the particle release curve, determining the substance within the fluid based on the determined part of the particle release curve.

In a further aspect of the present invention a binding method for cooperating with an analyzing method for determining a substance within a fluid is presented, the binding method comprising:

attaching particles to the substance within the fluid, binding the particles to a binding surface, if the particles have been attached to the substance, wherein the particles are bound to the binding surface with different kinds of binding, the analyzing method comprising:

sensing the particles on the binding surface, wherein a temporal sensing signal is generated depending on the bound particles, determining a particle release curve being indicative of a release of bound particles from the binding surface depending on the generated temporal sensing signal, determining a part of the particle release curve caused by particles bound to the binding surface via a predefined kind of binding based on a temporal behaviour of the particle release curve, determining the substance within the fluid based on the determined part of the temporal particle release curve.

In a further aspect of the present invention an analyzing method for cooperating with a binding method for determining a substance within a fluid is presented, wherein the binding method comprises:

attaching particles to the substance within the fluid, binding the particles to a binding surface, if the particles have been attached to the substance, wherein the particles are bound to the binding surface with different kinds of binding, the analyzing method comprising:

sensing the particles on the binding surface, wherein a temporal sensing signal is generated depending on the bound particles, determining a particle release curve being indicative of a release of bound particles from the binding surface depending on the generated temporal sensing signal, determining a part of the particle release curve caused by particles bound to the binding surface via a predefined kind of binding based on a temporal behaviour of the particle release curve, determining the substance within the fluid based on the determined part of the particle release curve.

In a further aspect of the present invention an analyzing computer program for determining a substance within a fluid is presented, wherein the computer program comprises program code means for causing a substance determining apparatus as defined in claim 1 to carry out the steps of the analyzing method as defined in claim 14, when the computer program is run on a computer controlling the substance determining apparatus.

It shall be understood that the substance determining apparatus of claim 1, the binding device of claim 11, the analyzing device of claim 12, the substance determining method of claim 13, the above described binding method, the analyzing method of claim 14 and the analyzing computer program of claim 15 have similar and/or identical preferred embodiments as defined in the dependent claims.

It shall be understood that a preferred embodiment of the invention can also be any combination of the dependent claims with the respective independent claim.

These and other aspects of the invention will be apparent from and elucidated with reference to the embodiments described hereinafter.

DETAILED DESCRIPTION OF EMBODIMENTS

Figure 1:
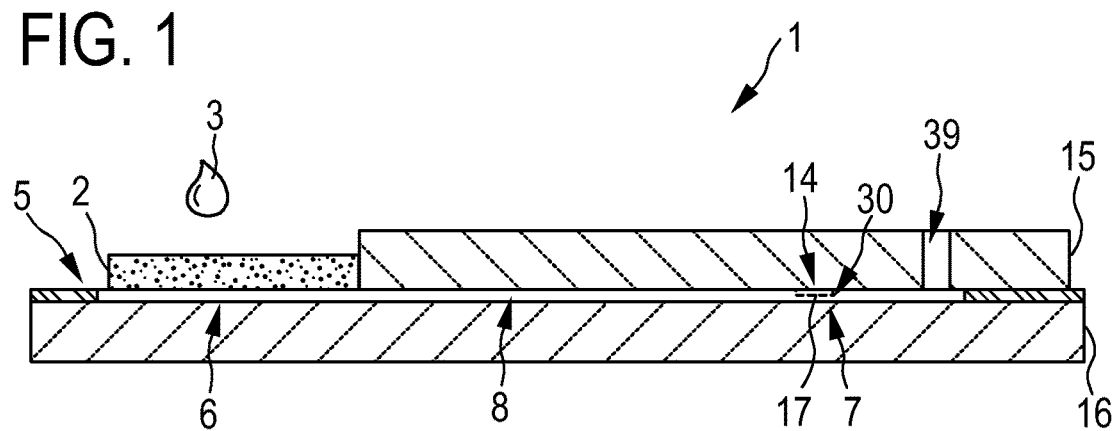
FIG. 1 shows schematically and exemplarily a cross-section of a binding device.

FIG. 1 shows schematically and exemplarily a binding device 1 for binding a substance which has to be determined within a fluid 3. The binding device 1 comprises a filter element 2 for filtering the fluid 3 and a capillary structure 5 for generating capillary forces. The capillary structure 5 is attached to the filter element 2 by using preferentially an adhesive. The capillary structure 5 is, in this embodiment, made of a double-sided tape which is adhesive on two sides.

The binding device 1 comprises a filtering location 6 at which the filter 2 is located and a sensing location 7 at which a substance within the fluid 3 is detectable, wherein the capillary structure 5 is formed such that the filtered fluid 3 is guided from the filtering location 6 to the sensing location 7 by capillary forces.

Figure 2:
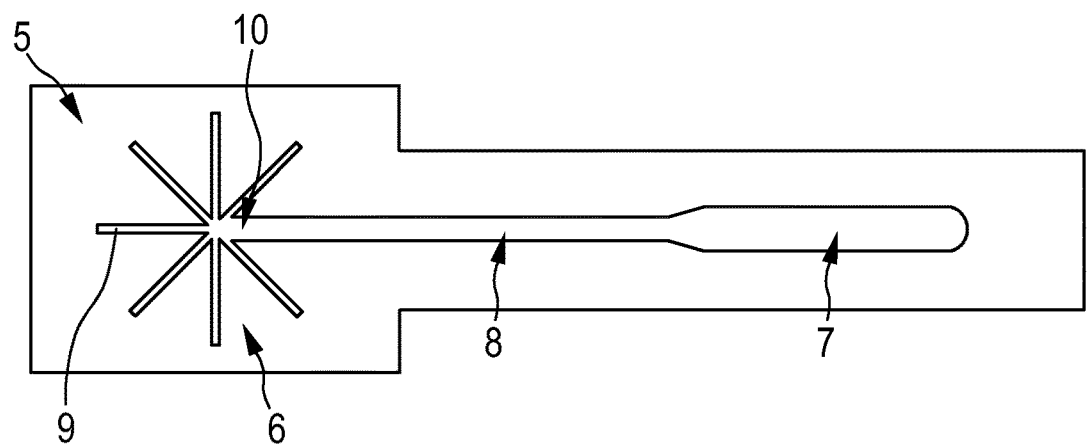
FIG. 2 shows schematically and exemplarily a capillary structure of the binding device.
Figure 3:
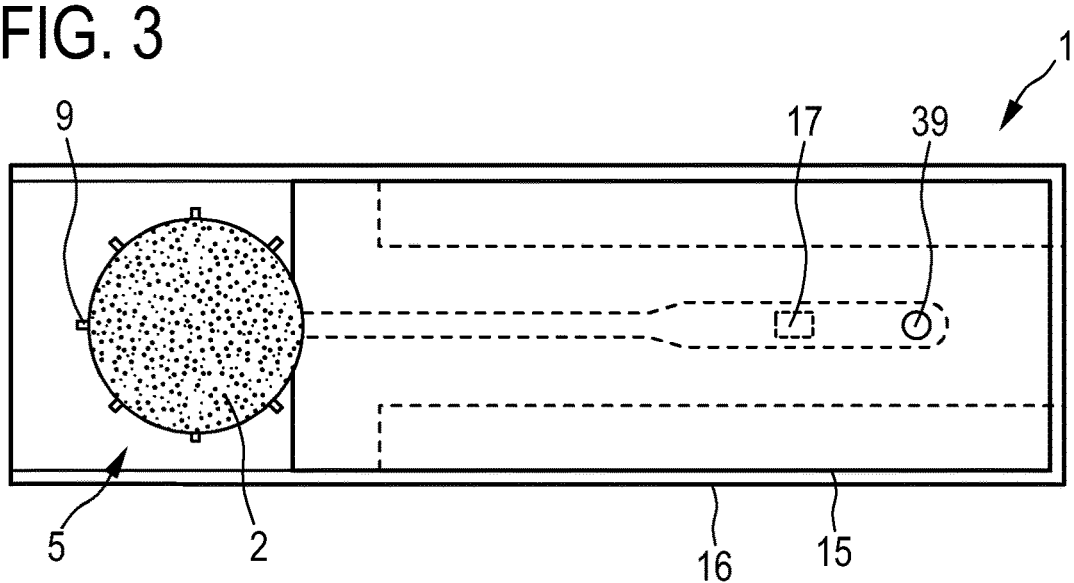
FIG. 3 shows schematically and exemplarily a top view on the binding device.

The capillary structure 5 comprises a collecting channel 8, which connects the filtering location 6 with the sensing location 7, and guiding channels 9 located at the filtering location 6, wherein the guiding channels 9 extend from an end of the connecting channel 8. In this embodiment the guiding channels 9 extend radially from the end 10 of the connecting channel 8. The capillary structure 5 is schematically and exemplarily shown in more detail in FIG. 2. FIG. 3 shows schematically and exemplarily a top view on the binding device 1 which is shown in a sectional view in FIG. 1.

The binding device 1 comprises a sensing cavity 14 which is located at the sensing location 7 and in which a substance of the fluid 3 is detectable. This sensing cavity 14 is formed by a first part 15 and a second part 16 of the binding device 1 together with the capillary structure 5. In addition, the first part 15 and the second part 16 form together with the capillary structure 5 the connecting channel 8. The first part 15 and the second part 16 are preferentially attached to each other via an adhesive, in particular, via the double-sided tape forming the capillary structure 5. The first part 15 and the second part 16 are plastic substrates which are injection molded and preferentially transparent to visible light. The first part 15 can be regarded as an upper substrate, closing element or cover element and the second part 16 can be regarded as a lower substrate or base element of the binding device 1. The first part 15 comprises a vent 39 for allowing a gas to leave the capillary structure 5.

In this embodiment, the filter element 2 is a blood separation filter and the binding device 1 forms a cartridge which is preferentially disposable. The binding device 1 is preferentially used in point-of-care diagnostics. The binding device 1 is preferentially adapted for detecting a low concentration biomarker in a sample of whole blood, in particular, in a finger prick sample of, for example, 25 µl. The sensing location 7 preferentially comprises an immunoassay. In particular, the sensing location 7 comprises a group 17 of particles for being attached to a substance within the fluid 3, wherein the group of particles mixes with the fluid 3, and the particles attach the substance within the fluid 3, if the fluid 3 is at the sensing location 7. The group 17 of particles can also be located between the sensing location 7 and the filtering location 6. The particles, which have attached the substance, are bound to a binding surface 30 at the sensing location 7. For binding the particles, which have attached the substance, the binding surface comprises binding elements at binding sites. The particles are bound to the binding surface 30 with different kinds of binding. Possible different kinds of binding will be described in more detail further below with reference to FIG. 5.

Figure 4:
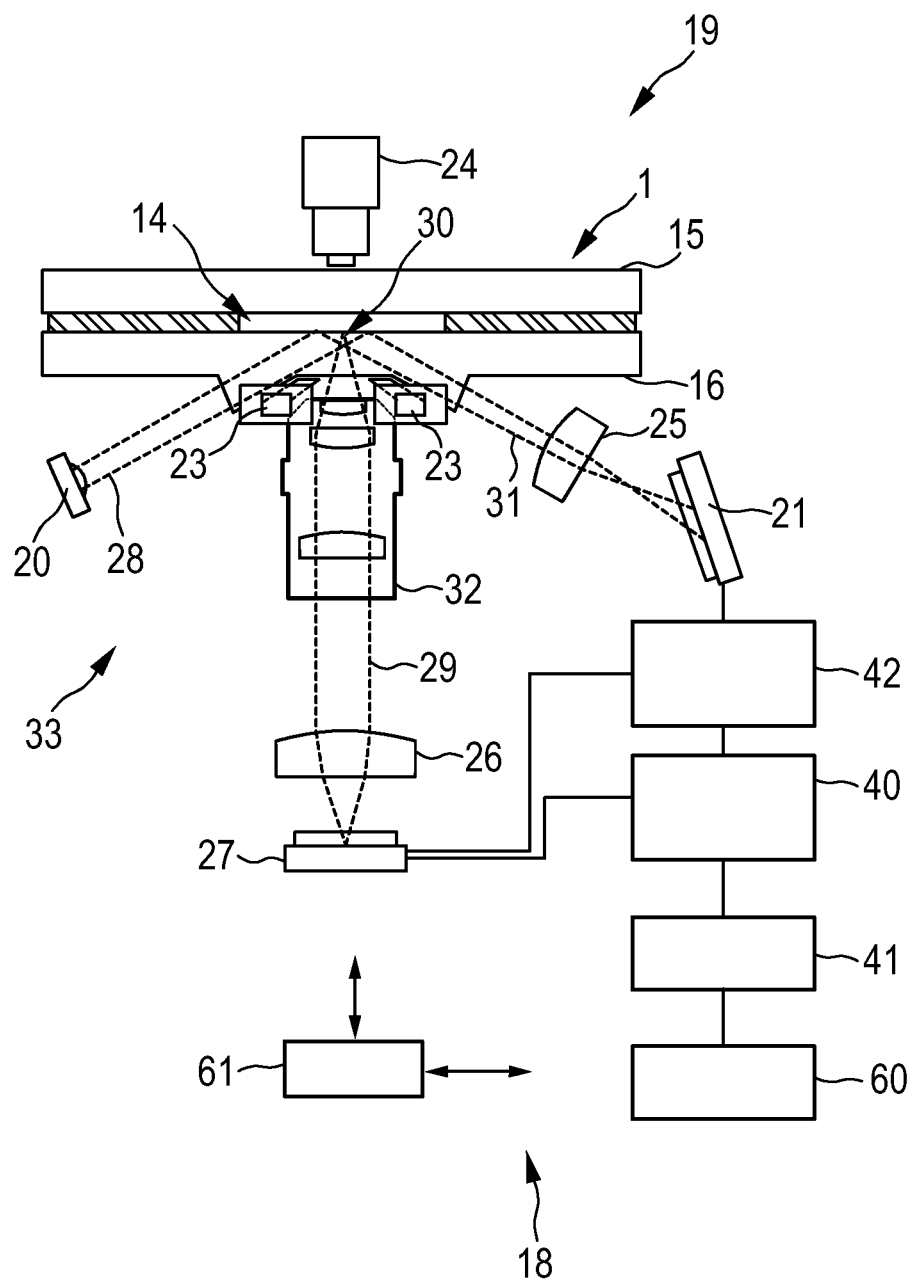
FIG. 4 shows schematically and exemplarily a substance determining apparatus comprising the binding device and an analyzing device.

FIG. 4 shows schematically and exemplarily a substance determining apparatus 19 comprising the binding device 1 and an analyzing device 18. The binding device 1 has been inserted into the analyzing device 18. The analyzing device 18 comprises a sensing unit 33 for sensing the particles on the binding surface 30, wherein the sensing unit 33 is adapted to generate a temporal sensing signal depending on the bound particles. A temporal sensing signal is a time dependent sensing signal being, for example, a FTIR signal or a DFM signal. The analyzing device 18 further comprises a particle release curve determination unit 42 for determining a particle release curve being indicative of a release of bound particles from the binding surface 30 depending on the generated temporal sensing signal, a binding determination unit 40 for determining a part of the particle release curve caused by particles bound to the binding surface 30 via a predefined kind of binding based on a temporal behaviour of the particle release curve, and a substance determination unit 41 for determining the substance within the fluid based on the determined part of the particle release curve. The predefined kind of binding is preferentially a specifically bound particle having attached the substance to be determined. Preferentially, the substance determination unit 41 is adapted to determine the amount and/or concentration of the substance within the fluid based on the determined part of the particle release curve.

The substance determining apparatus 19 is preferentially a magnetic biosensor, wherein the particles are magnetic beads, i.e. nanoparticles, which label the substance by being attached to the substance. For attaching the substance the magnetic beads are functionalized with an attaching element that can be attached to the substance being, for example, a specific analyte molecule. In this embodiment, the attaching element is an antibody. However, the attaching element can also be a protein, DNA, aptamer et cetera.

The sensing unit 33 comprises a force applying unit for applying a force to the particles for putting bindings between the particles and the binding surface 30 under stress, while sensing the particles. In this embodiment, the force applying unit comprises a magnetic unit 23, 24 for attracting the magnetic particles to the binding surface 30 and for pulling the magnetic particles away from the binding surface 30. The magnetic unit comprises a horseshoe magnet 23 being preferentially in a planar arrangement at one side of the binding device 1, if the binding device is inserted into the analyzing device, and a second magnet 24 being arranged on the opposite side of the binding device 1, if the binding device is inserted into the analyzing device.

The sensing unit 33 is preferentially adapted to sense the particles during a predefined sensing time, wherein the force applying unit is adapted to apply the force such that particles bound to the binding surface via the predefined binding are released mainly outside the sensing time and particles bound to the binding surface via another binding are released mainly inside the sensing time.

The sensing unit 33 further comprises a light source 20 being, for example, a light emitting diode or a laser for generating radiation 28 for being directed to the binding surface 30 for generating an evanescent field on the binding surface 30. The evanescent field on the binding surface 30 is influenced by the particles bound to the binding surface 30, thereby influencing a reflected light beam 31 comprising the light being total internally reflected at the cartridge surface, and a scattered light beam 29 comprising the light of the evanescent field scattered by the particles bound to the binding surface 30. The reflected light 31 is imaged by an objective 25 onto a first light detector 21 being preferentially a CCD camera. The scattered radiation is collected by a microscope objective 32 and imaged on a second detector 27 by an imaging lens 26. Also the second detector 27 is preferentially a CCD camera. The first detector 21 generates a temporal sensing signal which is provided to the particle release curve determination unit 42 for determining the particle release curve depending on the generated temporal sensing signal. Preferentially, the particle release curve determination unit 42 determines the temporal sensing signal in a washing phase as the particle release curve. The binding determination unit 40 determines a part of the particle release curve caused by particles bound to the binding surface via a predefined kind of binding based on the temporal behaviour of the particle release curve. The sensing signal of the first detector 21 is based on FTIR. The second detector 27 generates a position signal based on DFM. The position signal is provided to the binding determination unit 40.

The position signal is preferentially used for determining the positions of the particles. The microscope objective 32 is preferentially adapted to detect scattered light from a focal plane defining a detection plane. The scattered light from this detection plane is imaged onto a two-dimensional detection surface of the second detector 27. The resulting detected image being a temporal position signal generated by the second detector 27 shows the in-plane positions of the particles within the detection plane. The microscope objective 32 and the imaging lens 26 are preferentially adapted to allow the sensing unit 33 to move the detection plane with respect to the binding surface 30 such that the height positions of the particles with respect to the binding surface 30 can be determined. This allows determining the three-dimensional positions of the particles within the sensing cavity 14.

In the following the generation of FTIR sensing signals will shortly be described. If a beam of light reflects on the interface between a medium with a higher refractive index, for example the second part 16, and a lower refractive index, for example the fluid, there is a certain critical angle of incidence above which there is a situation of total internal reflection (TIR). The detection configuration (regarding refractive indices and angle of incidence) shown in FIG. 4 is such that there is total internal reflection of the incoming beam. Although the light is totally reflected in such a situation, there is still penetration of the light in a very thin layer of the medium with the low refractive index. This is called an evanescent field, the intensity of which decays exponentially in the low refractive index medium with a characteristic penetration depth of the order of the wavelength of the light. In practice the penetration depth is preferentially less than 0.5 micrometer. If magnetic particles are bound to the binding surface 30, the optical properties of this very thin first fluid layer of preferentially about 0.5 micrometer are changed leading to a reduction of the intensity of the reflected light beam. This is caused by absorption and scattering of the evanescent light (FTIR; frustrated total internal reflection). As a result the light intensity at the detector 21 decreases, whereas the light intensity at the detector 27 increases.

The sensing signal generated by the detector 21 is preferentially indicative of the change of the light intensity at the detector 21 and the position signal is preferentially indicative of the change of the light intensity at the detector 27.

As described above, the particle release curve determination unit can be adapted to determine the FTIR signal generated by the first detector 21 as the particle release curve. However, also the DFM signal generated by the second detector 27 can be used to determine the particle release curve. The second detector 27 generates images of the binding surface 30 at different times, which can also be regarded as the sensing signal, wherein an image shows at which positions on the binding surface 30 particles are bound at a time and wherein the particle release curve determination unit 42 is adapted to determine starting moments and ending moments of single binding events by comparing temporally consecutive images generated during the binding phase or the washing phase. The particle release curve determination unit 42 can be adapted to determine lifetimes of the bindings of the particles on the binding surface from the starting and ending moments, to generate a histogram of the lifetimes, and to determine the particle release curve depending on the generated histogram. In a preferred embodiment, the generated histogram is regarded as the determined particle release curve.

The substance determining apparatus 19 is preferentially adapted to provide a binding phase and a washing phase. In the binding phase the force applying unit forces the particles towards the binding surface, in order to allow the particles to be bound to the binding surface, and away from the binding surface in an alternating way. In the following washing phase the force applying unit applies a force to the particles, which urges the particles only away from the binding surface, thereby washing unbound particles away from the binding surface and putting the bindings between bound particles and the binding surface under stress. The stress can lead to a release even of bound particles.

The particle release curve can be determined in the binding phase or in the washing phase. If the particle release curve shall be determined in the binding phase, images of the binding surface are provided by the second detector at least at the times at which the unbound particles have been pulled away from the binding surface in the binding phase. Preferentially, consecutive images generated while the unbound particles are pulled away from the binding surface in the binding phase are compared for determining the lifetime of the bindings. If a particle is visible at a certain position in a first image and at the same position not in a preceding image, the time of a starting moment can be detected. If at a certain position with a second image a particle is visible and if at the same certain position in a subsequent image a particle is not visible, the time of an ending moment can be determined. The determined starting and ending times are used for determining lifetimes of single binding events, wherein a histogram of these lifetimes is formed and this histogram can be regarded as a determined particle release curve.

In the washing phase the FTIR sensing signal generated by the first detector 21 can be determined as the particle release curve. Alternatively or in addition, a histogram of lifetimes of single binding events can also be determined in the washing phase, wherein the resulting histogram can be regarded as the particle release curve determined by the particle release curve determination unit.

Figure 5:
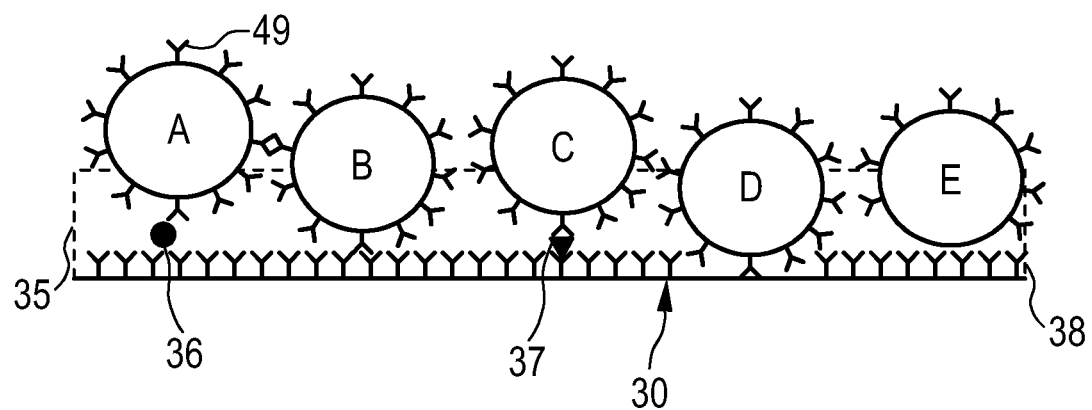
FIG. 5 shows schematically and exemplarily different kinds of binding to a binding surface.

FIG. 5 shows schematically and exemplarily different kinds of binding on the binding surface 30. In FIG. 5 the broken line 35 indicates schematically and exemplarily a height of the evanescent field which can be defined as a decay length $\zeta$ of the evanescent field. The particle indicated by A is specifically bound to the binding surface 30 via the attaching element 49, the substance 36 and the binding element 38. The particle B does not form a normal sandwich like the particle A, but is bound to the binding surface 30 via the attaching element 49 and the binding element 38, i.e. without a sandwiched substance.

The particle C is bound to the binding surface 30 via the attaching element 49, an element 37 not being the substance to be determined, i.e. not being the analyte, and the binding element 38. The particle D is directly bound to an exposed area on the binding surface 30 via the attaching element 49. This means, the binding surface 30 comprises the binding elements 38 for forming a normal sandwich as shown in FIG. 5 for the particle A. These binding elements 38 also bind particles B, C and E in the example shown in FIG. 5. However, the particle D is directly bound to the binding surface 30 via the attaching element 49.

In FIG. 5, only the particle A forms a normal sandwich. The particle A is therefore specifically bound to the binding surface 30. The other particles B, C, D, E do not form a normal sandwich and are therefore non-specifically bound to the binding surface 30.

A non-specific binding is preferentially any binding that is not dependent on the presence of the substance, i.e. on the presence of the specific analyte that has to be detect in the sample fluid. FIG. 5 illustrates differences between specific and non-specific bindings for a sandwich immunoassay. However, also other kinds of assay can comprise specific and non-specific bindings and the substance determining apparatus can also be used to determine specifically bound particles if another assay is chosen for determining the substance in the fluid.

Figure 6:
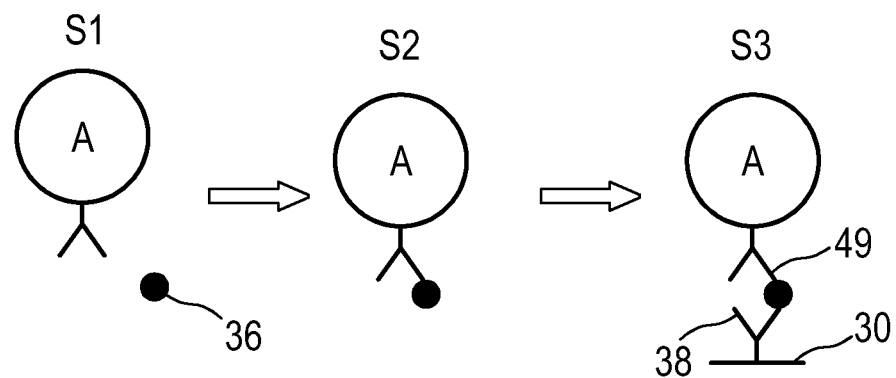
FIG. 6 shows schematically and exemplarily a specific binding process.

FIG. 6 illustrates schematically and exemplarily a normal specific sandwich immunoassay.

The particle A with the attaching elements 49 is mixed with the fluid comprising the substance 36 (step S1). Then, the attaching element 49 attaches the substance 36 (step S2), and the particle A with the attaching element 49 and the attached substance 36 specifically bounds to the binding surface 30 via a binding element 38 (step S3).

The different kinds of binding are generally related to different temporal behaviours, in particular, to different time constants of exponential decays of the particle release curve. A part of the particle release curve caused by particles bound to the binding surface via a predefined kind of binding like the binding of particle A in FIG. 5 can therefore be determined based on the temporal behaviour, in particular, based on the time constants, of the particle release curve.

The binding determination unit 40 is preferentially adapted to determine time constants of the particle release curve, wherein the time constants are indicative of kinds of binding of particles bound to the binding surface 30, and wherein the binding determination unit 40 is adapted to determine a part of the particle release curve, which decays with at least one of the determined time constants, as the part of the particle release curve caused by particles bound to the binding surface 30 via the predefined kind of binding. The predefined kind of binding can be a specific binding of a particle on the binding surface 30. Thus, the binding determination unit 40 can be adapted to determine a part of the particle release curve caused by particles bound to the binding surface by specific bindings based on the respective determined time constant, wherein the substance determination unit 41 is adapted to determine the substance within the fluid based on the determined part of the particle release curve.

The particle release curve is preferentially regarded as being comprised of a superposition of decaying exponential functions with different time constants. A part of the particle release curve caused by a certain kind of binding is preferentially one or a combination of several of the exponentially decaying curves having one or several time constants being indicative of the certain kind of binding.

The determination of a substance within a fluid based on specifically bound particles will in the following exemplarily be described in more detail.

The particle release curve consists of a part which contains the desired information and a part which contains irrelevant information for the determination of the substance. The desired information is the part caused by the specifically bound particles and the irrelevant information is the part caused by the non-specifically bound particles. In order to be able to determine the first part of the particle release curve caused by specifically bound particles, it has to be separated from the part of the particle release curve caused by the non-specifically bound particles.

The particles are coupled to the binding surface by means of molecular bonds, i.e. bindings. A molecular bond consists of many interactions on the atomic level such as dipole-dipole or electrostatic interactions. Specific bonds often involve many different atomic interactions because the shape of one complex molecule like a protein fits exactly to the shape of another complex molecule like the antibody. Non-specific bonds often involve less atomic interactions because of the absence of an exact fit of the molecules. The binding strength of a specific bond is therefore often larger, in particular, much larger, than the binding strength of a non-specific bond. This binding strength determines a chemical reaction constant $k_{off}$ of the binding, wherein the chemical reaction constant specifies the release rate of the bond in events per second. For example, a strong bond will have a low release rate of, for instance, $10^{-5}$ s$^{-1}$, while a weak bond will have a high release rate of, for instance, $10^{-2}$ s$^{-1}$. This difference in the release rates and, thus, in $k_{off}$ can be used to discriminate between specific and non-specific bonds. If the value of $k_{off}$ is determined without the presence of additional forces applied, this value is denoted as the chemical reaction constant $k_{off,chem}$. The chemical reaction constant is characteristic of the chemical bond.

Figure 7:
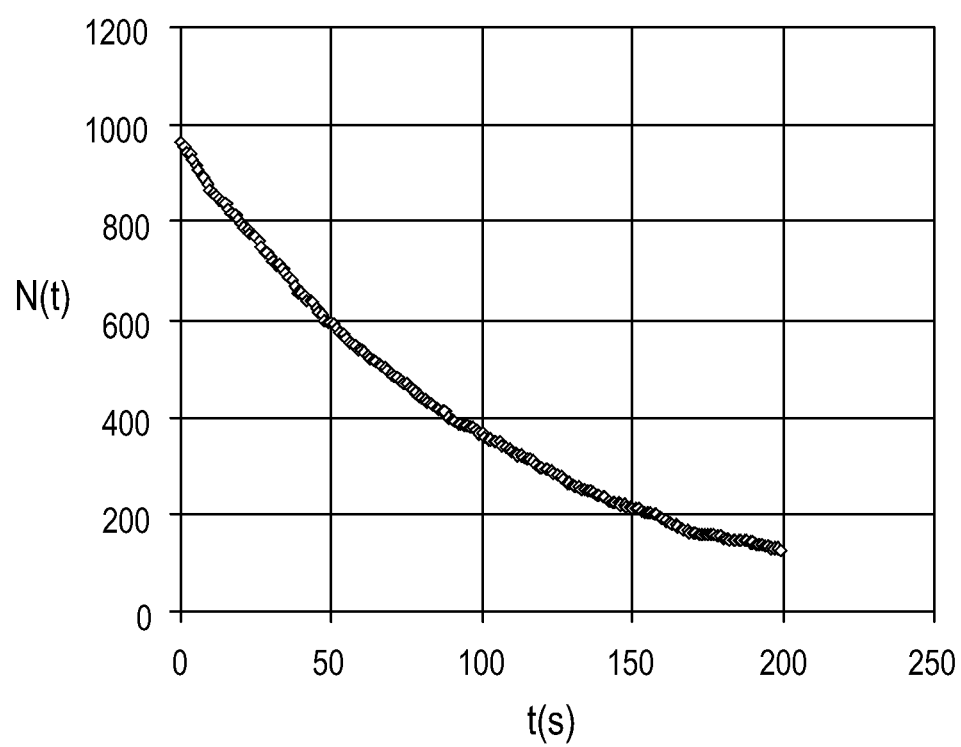
FIG. 7 shows schematically and exemplarily a particle release curve if one kind of binding is present.

The chemical reaction constant $k_{off}$ determines the time constant of the particle release curve. In this embodiment, the chemical reaction constant $k_{off}$ is defined as the inverse of the time constant of the particle release curve. FIG. 7 shows schematically and exemplarily a monoexponential decay of the particle release curve, which can be observed, if the particles are bound to the binding surface via one kind of binding only. If the value of $k_{off,chem}$ is small, it will take a long time before the majority of the particles have been released from the binding surface by natural means. For example, it can take $10^5$ s before most of the particles have been released. Such a time is much too long in a Point-Of-Care setting.

By stressing the bonds by means of an external force the release rate can be increased. The combination of the chemical reaction constant $k_{off,chem}$ and an external force F to stress the bonds results in a new effective release rate $k_{off,eff}$. If the external force F is known, the chemical reaction constant $k_{off,chem}$ can be calculated from the effective $k_{off,eff}$ in accordance with following equation:

$$k_{off,eff} = k_{off,chem} \cdot c(F), \quad (1)$$

where c(F) is a correction factor which depends on the magnitude of the force. The function c(F) can be a simple linear or exponential function with only one parameter, wherein the parameter can be estimated or determined by means of calibration. The calibration can be performed by applying known forces to the particles, determining the effective reaction constant $k_{off,eff}$ and by dividing the determined effective reaction constant by a known chemical reaction constant $k_{off,chem}$. In this embodiment, the reaction constant is preferentially defined as the inverse time constant of the exponential decay of the particle release curve.

In particular, the correction factor c(F) can be expressed by following equation:

$$c(F) = e^{\beta F}, \quad (2)$$

wherein β is a proportionality factor being a constant which can experimentally be determined for the respective kind of binding.

By applying a corresponding magnitude of force it is possible to bring the effective release rate, i.e. the effective reaction constant, in a range where a full release of particles can be achieved in a suitable sensing time of, for example, about 100 s. By measuring the decay rate of the particle release curve the value of the effective reaction constant can be determined, wherein the chemical reaction constant is then obtained by using equation (1). This chemical reaction constant or the corresponding time constant being the inverse of the chemical reaction constant, can be used for determining a part of the particle release curve, in particular, of the generated FTIR sensing signal, caused by specifically bound particles. The chemical reaction constant can be regarded as a fingerprint of the respective kind of binding.

The total particle release curve is partly caused by specifically bound particles with a chemical reaction constant $K_{off,chem,spec}$ and partly caused by non-specifically bound particles with a chemical reaction constant $k_{off,chem,non-spec}$. The binding determination unit and the substance determination unit are preferentially adapted to determine which fraction of the particle release curve is caused by specifically bound particles depending on the chemical reaction constants, i.e. on the corresponding time constants of exponential decay curves fitted to the particle release curve.

In order to illustrate a temporal behaviour of a particle release curve in the following a view examples with increasing difficulty will be given.

In a first example, the population of particles bound to the binding surface consists of particles with only one kind of binding, i.e. with only one type of bond. An external force is not applied. The reaction constant is equal to $k_{off,chem}$ and has a constant value, i.e. the reaction constant is independent of time. If at a starting time t=0, a sensing signal $N_0$ is detected after some time the number of particles on the binding surface becomes less because continuously bonds are broken, resulting in the particle release curve. The sensing signal N(t) after time t can be described by following equation:

$$N(t) = N_0 \cdot e^{-k_{off,chem} \cdot t}. \quad (3)$$

By means of fitting equation (3) with fitting parameters $N_0$ and $k_{off,chem}$ to the particle release curve both values can be determined. If the reaction constant is very low, the decrease of the particle release curve is very low and the sensing time has to be very large before a reliable fitting procedure can be performed. In order to decrease the sensing time, the reaction constant can be enhanced by stressing the bond with an external force. This situation is described in the following second example.

In the second example, the population of particles bound to the binding surface consists of particles with only one kind of binding, in particular, with only one type of bond. To enhance the reaction constant from the low chemical value $k_{off,chem}$ to a larger effective value $k_{off,eff}$ a force is used to stress the bonds. By means of this action the desorption is enhanced to such a level that a noticeable decrease in the number of bound particles on the binding surface can be obtained within the sensing time. In this example, a magnetic force is applied to the particles, although in general also other types of forces could be used such as fluidic forces. The application of a magnetic force to enhance the release rate can be called magnetic force discrimination. The magnetic force can be generated in several ways.

One way of generating a force is to use an external magnetic unit, which generates both a magnetic field and a magnetic field gradient, like the magnetic unit 23, 24 described above with reference to FIG. 4. The combination of magnetic field and magnetic field-gradient exerts a magnetic force on the particles, which are preferentially (super) paramagnetic beads, which can be used to pull the particles away from the binding surface. In this case the force is likely to be time-independent. The particle release curve as a function of time can then be described by following equation:

$$N(t) = N_0 \cdot e^{-k_{off,eff} \cdot t}. \quad (4)$$

Again, by means of fitting, both $N_0$ and $k_{off,eff}$ can be determined.

Since the force F is known or can be calculated by using equation (6) mentioned above and since the dependence of the correction factor c(F) on the force F is known from calculations or from calibration procedures, the chemical reaction constant $k_{off,chem}$ can be determined in accordance with following equation:

$$k_{off,chem} = \frac{k_{off,eff}}{c(F)}. \quad (5)$$

The magnetic force F exerted onto a particle by the magnetic field and the magnetic field gradient can be estimated by using following equation:

$$\vec{F}=(\vec{m}(\vec{B})\cdot\vec{\nabla})\cdot\vec{B}, \quad (6)$$

wherein $\vec{m}(\vec{B})$ is the field-dependent magnetic moment of the particle and $\vec{B}$ is the applied magnetic induction. The magnetic field and the magnetic field gradient are preferentially adapted such that a force is generated for pulling the particles vertically with respect to the binding surface away from the binding surface. Since the magnetic properties of the particles and the magnetic field are known, the vertical force on the particles can be calculated. The magnetic properties of the particles can be determined by means of a Vibrating Sample Magnetometer (VSM) measurement and the magnetic field and magnetic field gradient can be determined from finite-element calculations and calibrated by means of a magnetic field sensor. In this example, the determination of the effective reaction constant $k_{off,eff}$ can be corrected for the known applied force, wherein a value for the chemical reaction constant $k_{off,chem}$ can be derived in accordance with equation (5).

Figure 8:
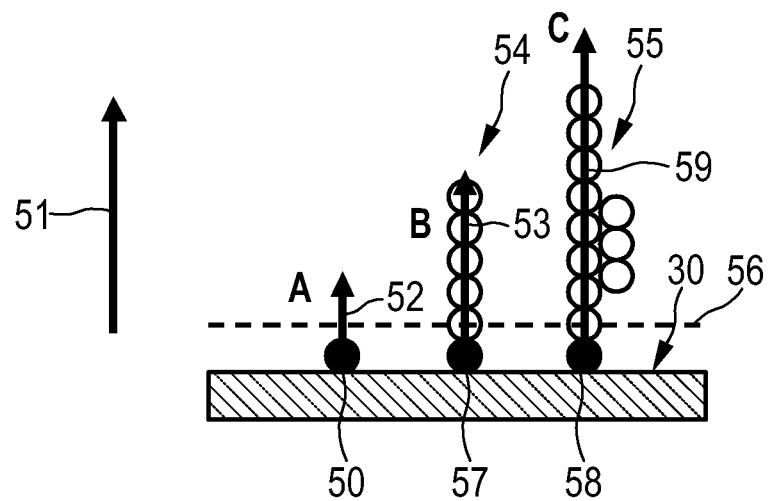
FIG. 8 shows schematically and exemplarily a clustering of free particles if a magnetic field is applied.

Besides particles, which will bind to the binding surface, there are also particles which did not capture a target molecule of the substance and which are therefore not able to specifically bind on the binding surface. A fraction of these particles will non-specifically bind to the binding surface, but another fraction of these particles will remain within the fluid as free particles. Particularly at low concentrations the majority of the particles will be free particles. When a vertical magnetic field is applied, the magnetic particles, which are preferentially (super)paramagnetic particles, become magnetized with their magnetic moment parallel to the applied magnetic field. Like small magnets they will magnetically attract each other and form chains in the direction of the applied vertical magnetic field. This is schematically and exemplarily illustrated in FIG. 8. In FIG. 8, the letter A indicates a situation showing a single particle 50 without a cluster of further free particles. A force 52 is applied to the single particle 50. Another situation showing a bound particle 57 with a chain 54 of free particles is indicated by B. The interaction of the particles in the chain 54 and the external magnetic force result in a force 53 for pulling the particle 57 away from the binding surface 30. A situation showing a larger cluster 55 of free particles attached to a bound particle 58 is indicated by C, wherein the resulting force is indicated by the arrow 59.

In the situations B and C the force which is exerted on the bound particle is substantially equal to the sum of the forces on the individual particles in the chain 54 or the cluster 55, respectively, wherein the forces between the particles are much larger than the bond of the bottom particle to the binding surface 30.

The sensing unit 33 can move the detection plane with respect to the binding surface 30 as described above with reference to FIG. 4. The detection plane is indicated in FIG. 8 by reference number 56. By moving the detection plane 56 in a vertical direction, the chain 54 and the cluster 55 can vertically be scanned for generating a position signal. The resulting position signal can be provided to the binding determination unit for determining the arrangement of the individual particles in the chain 54 or in the cluster 55, respectively. Moreover, height calibrated information from a focusing servo connected to the microscope objective 32 and the imaging lens 26 can be used for determining a height of a chain or of another kind of cluster. Since the binding determination unit is preferentially adapted to determine for each height of the detection plane the two-dimensional positions of the particles within the detection plane, for each particle of a cluster, in particular, of a chain, the three-dimensional position can be determined. These positions can be used to determine the total magnetic force applied to the respective bound particle. Preferentially, an average force per bound particle is determined as an average over the total magnetic forces applied to the bound particles. This average force per bound particle is preferentially used for calculating the correction factor c(F). The signal generated by the second detector 27 can therefore be used for determining the positions of the particles for determining the total magnetic force applied to the respective bound particle and the signal generated by the second detector 27 can also be used as a sensing signal for determining a particle release curve in the binding phase or in the washing phase as described above.

Besides an external force a magnetic interaction force between the particles can be used for putting the bindings under stress. The advantage of using the particle-particle interactions is that is it easier to generate large forces. Therefore, a larger enhancement of the release rate, i.e. the desorption constant, can be obtained. In order to create forces between the particles itself, it is sufficient to provide a magnetic field. A magnetic field gradient is not required. The magnetic field magnetizes the magnetic particles, which start to emit their own magnetic field and field gradient. The magnetic induction from a particle can be calculated using the dipole approximation according to following equation:

$$\vec{B} = \frac{\mu_0}{4\pi}\left[-\frac{\vec{m}}{r^3} + \frac{3(\vec{m}\cdot\vec{r})\vec{r}}{r^5}\right], \quad (7)$$

wherein $\vec{m}$ is the external field-dependent magnetic moment of the particle and $\vec{r}$ is the distance to the particle. This dipole field and field gradient lead to a mutual interaction between the particles with the generation of large forces. Since the magnitude of the external magnetic field and the magnetic properties of the particles are known, the magnetic moment of the particle and the magnetic forces acting on a particle can be calculated.

As already mentioned above, the sensing unit 33 is adapted to determine the positions of the particles from the generated position signal, i.e. from the generated DFM signal. Since the positions of the particles are known, also the distances $\vec{r}$ between the particles are known. This allows the binding determination unit to determine the magnetic force applied to the respective individual bound particle by calculating the magnetic field and field gradient of a particle in accordance with equation (7) and by vectorally adding the corresponding magnetic forces acting on the respective individual bound particle. Such a determination is not very complicated and could even be performed in real time. A real time determination has the advantage that modifications to the binding surface configuration, for example, because particles are released from the binding surface, can immediately be taken into account in the determination of the magnetic force acting on the bound particles. For every broken binding the history of the time-dependent magnetic force can be determined. The binding determination unit can be adapted to use the determined time-dependent magnetic force for determining a time-dependent average magnetic force which can be used to determine a time-dependent correction factor c(F)=c(F(t)), wherein the correction factor is used for correcting a measured effective reaction constant $k_{off,eff}$, in order to yield a more accurate estimate for the chemical reaction constant $k_{off,chem}$ and to allow an easier data analysis.

Figure 9:
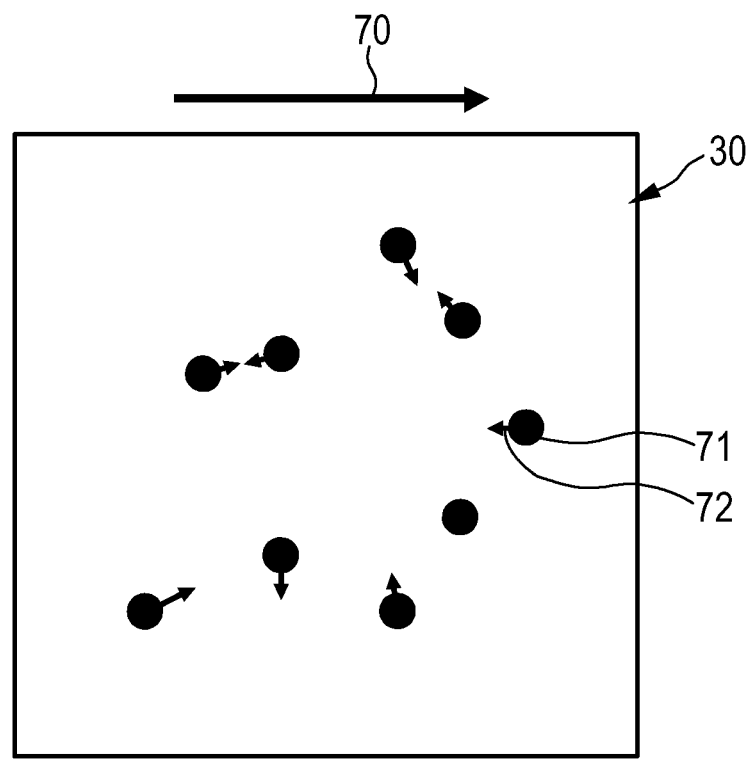
FIG. 9 shows schematically and exemplarily particle-particle interactions on a binding surface.

FIG. 9 shows schematically and exemplarily a top view on a binding surface 30 comprising several bound particles 71. Due to the magnetic field 70 the particles 71 are magnetized and start exerting forces to each other. The magnitude of the force 72 on an individual particle 71 is caused by the vectorial sum of all particle-particle interactions.

As already mentioned above, the particle-particle interaction force is dependent on the distance between the particles. During the process of removing particles from the surface, the average distance between the particles changes continuously. The changing average distance causes an interaction force which changes in time. The effective reaction constant $k_{off,eff}$ and the corresponding time constant are therefore also functions of time. An estimate of the temporal behaviuor of the force can be made by analyzing each individual image of the binding surface. Within each image the positions of the particles are determined and from the positions the interaction force between the particles is calculated using equation (7). Integrating the force over all particles on the surface, an average force for that image can be determined. By analyzing subsequent images in time, a temporal average force F(t) per particle can be determined which can be used for the correction factor c(F(t)). The average can be a weighted average, wherein each particle receives the same weight or wherein, for example, the forces determined for the particles are weighted depending on their magnitude. For example, a larger force can receive a larger weight than a smaller force.

The particle release curve can in this case be expressed by following equation:

$$N(t)=N_0 \cdot e^{-k_{off,chem} \cdot c(F(t)) \cdot t}. \qquad (8)$$

Due to the time-dependent argument in the exponential function N(t) is not a clean exponential function anymore.

Figure 10:
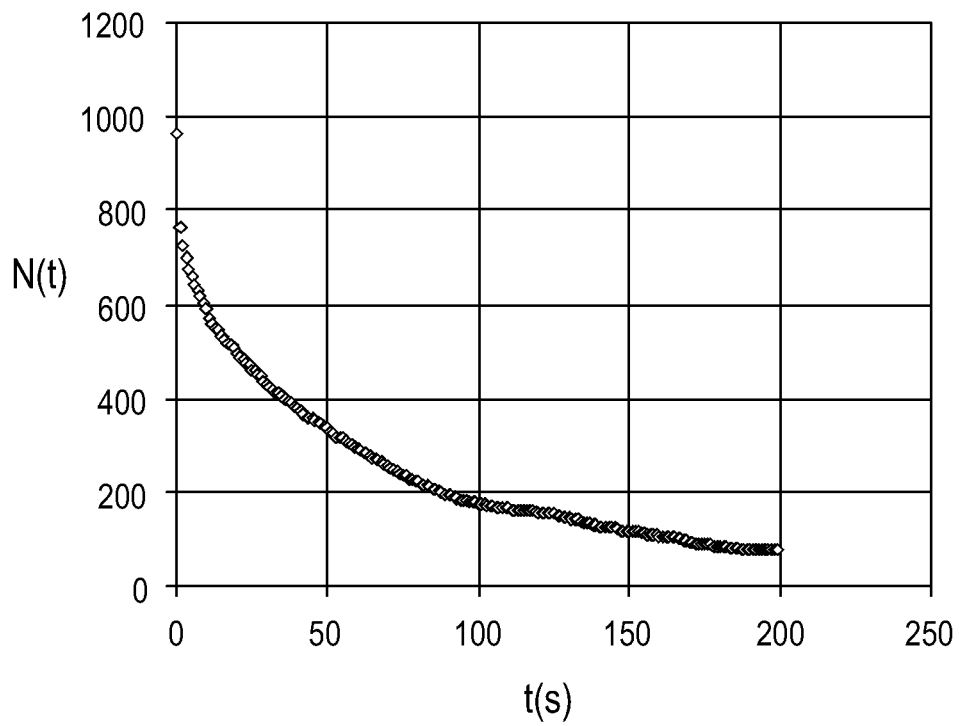
FIG. 10 shows schematically and exemplarily a particle release curve if particle-particle interactions are present.

An example of a particle release curve where the particle release is enhanced by means of particle-particle interaction is exemplarily shown in FIG. 10. FIG. 10 shows the particle release curve depending on the time in seconds for one kind of particles of a substance and with a chemical reaction constant of $10^{-2}$ $s^{-1}$. The particle release curve shown in FIG. 10 looks like it comprises several time constants, which is basically correct, although the corrected time constant, i.e. the corresponding chemical reaction constant $k_{off,chem}$, remains the same during the sensing time. The binding determination unit can be adapted to determine the time depending force F(t) and the correction factor c(F(t)) as described above depending on the positions of the particles and to determine the corrected chemical reaction constant $k_{off,chem}$, which is equal to the inverse corrected time constant, by fitting equation (8) to the particle release curve. The correction factor c(F(t)) is preferentially linear in time t and can be determined by, for example, calibration as described above.

If several kinds of binding are present, the several kinds of binding generally relate to different reaction constants. In an embodiment, a first kind of binding is a specifically bound particle and a second kind of binding is a non-specifically bound particle. Both, the specifically bound particles and the non-specifically bound particles contribute to the particle release curve. The substance determining apparatus is preferentially adapted to determine the part of the particle release curve caused by the specifically bound particles only.

Figure 11:
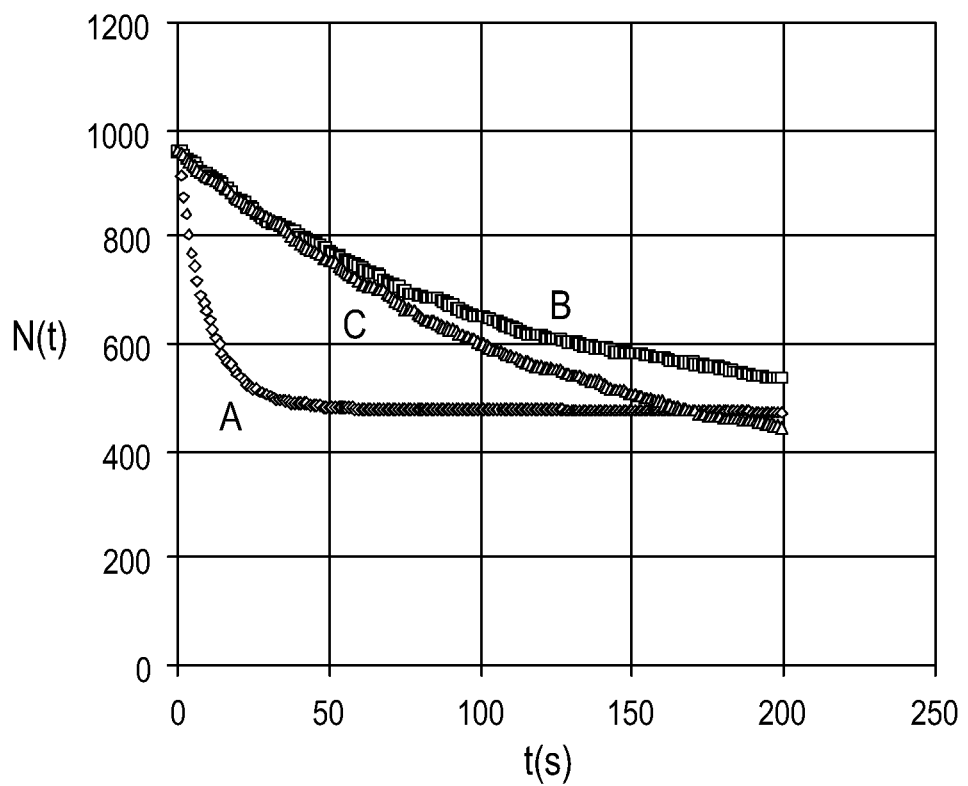
FIG. 11 shows schematically and exemplarily several particle release curves if two different kinds of binding are present.

In the following the chemical reaction constant of specifically bound particles is denoted by $k_{off,chem,spec}$ and the chemical reaction constant of non-specifically bound particles is denoted by $k_{off,chem,non-spec}$. If there is a large difference between these two reaction constants, for example, a difference of about three orders of magnitude, and if a part of the particle release curve caused by one of the specifically bound particles and the non-specifically bound particles relates to a relatively large signal change within the sensing time, the decrease of the particle release curve consists of two exponential decays with significantly different time constants. This allows the binding determination unit to distinguish the part of the particle release curve caused by specifically bound particles from the part of the particle release curve caused by non-specifically bound particles in a simple way. For example, if the non-specific chemical reaction constant is much larger than the specific chemical reaction constant such that the non-specifically bound particles are released very fast at the beginning of the sensing time, the part of the particle release curve caused by specifically bound particles can immediately be determined from the level of the tail of the particle release curve at the end of the sensing time. A corresponding particle release curve is shown in FIG. 11 as curve indicated by A. The inflection point of the curve indicated in FIG. 11 by A could be used to terminate the particle release of the non-specifically bound particles.

FIG. 11 shows schematically and exemplarily several particle release curve which correspond to specifically bound particles and non-specifically bound particles having different reaction constants, i.e. different time constants. The particle release curve indicated by A corresponds to a difference of the reaction constants of three orders of magnitude, the particle release curve indicated by B corresponds to a difference of the reaction constants of two orders of magnitude and the particle release curve indicated by C corresponds to a difference of the reaction constants of one order of magnitude.

If the difference between the specific chemical reaction constant $k_{off,chem,spec}$ and the non-specific chemical reaction constant $k_{off,chem,non-spec}$ is equal or less than two orders of magnitude, the distinction between the two exponential functions is less clear. The curves look more smooth and it is almost impossible to tell by eye that there are two distributions present. A fitting procedure is preferred to determine the part f of the particle release curve caused by specifically bound particles. In this case the particle release curve can be described by following equation:

$$N(t)=N_0 \cdot (f \cdot e^{-k_{off,chem,spec} \cdot t} + (1-f) \cdot e^{-k_{off,chem,non-spec} \cdot t}). \qquad (9)$$

In an embodiment, the binding determination unit is preferentially adapted to fit equation (9) to a particle release curve, wherein the fitting parameters are f, $k_{off,chem,spec}$ and $k_{off,chem,non-spec}$, if an external force is not applied to the particles for putting the bindings under stress. The substance determination unit then determines the amount or concentration of the substance within the fluid based on the specific part $N_{spec}(t)$ of the particle release curve defined by following equation:

$$N_{spec}(t)=N_0 \cdot f. \qquad (10)$$

The variable $N_0$ indicates the particle release curve at the beginning of the sensing time, i.e. at t=0.

As already mentioned above, during the sensing time a force can be applied to the bound particles, in order to put the bindings between the particles and the binding surface under stress. This increases the reaction constants, wherein the forces are preferentially applied such that a change of the particle release curve caused by the most weakly bound particles is detectable during the sensing time. Preferably, the forces are applied such that the desorption of the non-specifically bound particles is mainly within the sensing time, while the desorption of the specifically bound particles is mainly outside the sensing time. The particle release curve $N(t)$ as a function of time can then be described by following equation:

$$N(t) = N_0 \cdot (f \cdot e^{-k_{off,chem,spec} \cdot c(F) \cdot t} + (1-f) \cdot e^{-k_{off,chem,non-spec} \cdot c(F) \cdot t}) \quad (11)$$

As already mentioned above, depending on the kind of force applied to the particles, the force F can be independent of the time or the force F can depend on the time. In both cases the binding determination unit can determine the force F and the correction factor $c(F)$. The binding determination unit is then preferentially adapted to fit equation (11) to the generated particle release curve, wherein the fitting parameters are $f$, $k_{off,chem,spec}$ and $k_{off,chem,non-spec}$, i.e. $f$, and the corrected time constants being the inverse of the chemical reaction constants. The binding determination unit is then further adapted to determine the part of the particle release curve caused by particles bound to the binding surface via a specific binding in accordance with equation (10), and the substance determination unit is adapted to determine the amount and/or concentration of the substance within the fluid based on this determined part of the particle release curve. For determining the amount and/or concentration of the substance the substance determination unit preferentially comprises assignments between the part of the particle release curve caused by specifically bound particles and the amount and/or concentration of the substance within the fluid. These assignments can be determined by performing calibration procedures with known amounts and/or concentrations of specifically bound particles. The assignments can be stored in the substance determination unit in tabular form or as functions.

Although the above described embodiments are mainly related to the determination of a part of the particle release curve caused by specifically bound particles and to the determination of the substance within the fluid based on this determined part of the particle release curve, the substance determining apparatus can also be adapted to determine different substances within the same fluid, because different kinds of particles for attaching different substances generally comprise different reaction constants leading to different time constants of the particle release curve. The resulting temporal behaviour of the particle release curve can therefore be used to determine the different substances within the fluid in accordance with equations (9) to (11). In particular, the particles can comprise first particles for being attached to a first substance within the fluid and second particles for being attached to a second substance within the fluid, and the binding surface can be adapted to bind the first particles, if the first particles have been attached to the first substance, and to bind the second particles, if the second particles have been attached to the second substance, wherein the first particles are bound to the binding surface with a first kind of binding and the second particles are bound to the binding surface with a second kind of binding. The sensing unit can be adapted to sense the first particles and the second particles on the binding surface, wherein the sensing unit is adapted to generate a temporal sensing signal depending on the bound first and second particles, the particle release curve determination unit can be adapted to determine a particle release curve being indicative of a release of the bound first and second particles from the binding surface depending on the generated temporal sensing signal, and the binding determination unit can be adapted to determine a first part of the particle release curve caused by first particles bound to the binding surface via the first kind of binding and a second part of the particle release curve caused by second particles bound to the binding surface via the second kind of binding. In this case, the substance determination unit is adapted to determine the first substance within the fluid based on the determined first part of the particle release curve and the second substance within the fluid based on the determined second part of the particle release curve.

In general, the binding determination unit can be adapted to determine one or several parts of the particle release curve, which correspond to one or several kinds of binding, by using a linear combination of exponential decay curves with respective chemical reaction constants, i.e. time constants which are preferentially corrected, if the reaction constants and the time constants are influenced by a force, and by fitting the linear combination of exponential decay curves to the temporal generated sensing signal. Equations (9) and (11) show examples of such a linear combination, wherein in these examples the linear combination comprises two exponential decay curves.

The fitted time constants can be compared with time constants which are known to relate to certain kinds of binding. For example, experiments carried out on samples which only contain specific or non-specific bindings can be used to determine the time constants for those bindings. For example, only non-specific bindings can be made on the binding surface by not introducing the substance in the fluid, and only specific bindings can be made by using high concentrations of the substance within the fluid, at which the amount of non-specific bindings is negligible.

As already mentioned above and again referring to FIG. 4, the sensing unit 33 is preferentially adapted such that position signals caused by single particles can be distinguished using the scattered light 29 collected by the microscope objective 32 and imaged onto the second light detector 27 by the imaging lens 26. The second light detector 27 comprises a two-dimensional detection surface 30 for generating images of the binding surface at different times. Moreover, the microscope objective 32 and the imaging lens 26 are preferentially adapted to move the focal plane defining a detection plane in a height direction with respect to the binding surface 30 in order to scan the particles in different distances with respect to the binding surface 30. The generated DFM position signal is therefore preferentially used to determine the positions of the particles. These positions are preferentially used by the binding determination unit for determining the forces applied to the respective particles and for determining the correction factor $c(F)$ depending on the determined forces. The correction factor $c(F)$ is then used by the binding determination unit for determining the part of the particle release curve, caused by particles bound to the binding surface via a predefined kind of binding, wherein the predefined kind of binding is preferentially a specific binding of a particle having attached a substance to be determined. The substance determination unit is preferentially adapted to determine the substance within the fluid based on this determined part of the sensing signal.

As preferentially performed in all described embodiments, after the fluid has mixed with the particles for allowing the particles to attach the substance within the fluid, the particles are attracted to the binding surface for allowing the particles to be bound on the binding surface in a binding phase. In a following washing phase, the particles which are not bound to the binding surface are pulled away from the binding surface. As already mentioned above, in the binding phase alternating forces can be applied to the particles pointing towards the binding surface and pointing away from the binding surface. The sensing time can be located in the binding phase or in the washing phase depending on the kind of phase in which the sensing signal is generated, which is used for determining the particle release curve.

Optionally, during sensing the particles on the binding surface, the bindings between the particles and the binding surface are put under stress by using the force applying unit. The force applying unit 23, 24 is, in this embodiment, a magnetic unit for attracting the particles to the binding surface or for pulling the particles in a direction away from the binding surface. However, magnetic forces can also be applied to change the orientation of the particles for putting the bindings under stress.

This can be performed due to non-ideal magnetic properties, because the magnetic moment of an ideally superparamagnetic particle would always align with the field, thus making induction of an orientation change impossible. Non-ideal magnetic properties are, for example, a small permanent moment, magnetic grains with relatively long relaxation times or magnetic anisotropy. The force applying unit can be preferentially adapted to apply an orientation change to the bound particles such that the height of the bound particles, i.e. the distance of the bound particles to the binding surface, is modified. Thus, by applying an orientation change to the bound particles the distance between the particles bound to the binding surface and the binding surface can be modified for modifying the stress apparatus to the bindings. The particles can be magnetic particles having a diameter between 500 nm and 1000 nm and can be composed of a combination of polystyrene and a magnetic material.

Figure 12:
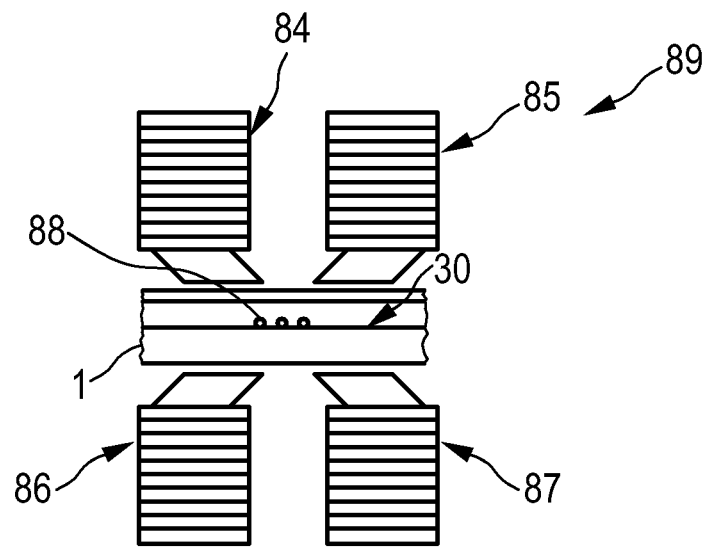
FIG. 12 shows schematically and exemplarily a force applying unit for applying magnetic forces to particles such that the orientation of the particles is modified.

FIG. 12 shows schematically and exemplarily a force applying unit 89 for applying magnetic forces to the magnetic particles 88 such that the orientation of the magnetic particles can be modified, thereby modifying the height of the magnetic particles 88 bound to the binding surface 30. The force applying unit 89 comprises four electromagnets 84, 85, 86, 87 for applying the magnetic field in the desired direction to the magnetic particles 88.

The force applying unit 89 is adapted to magnetically orient the magnetic particles 88, which are, in this embodiment, non-ideally superparamagnetic particles, for putting the bindings under stress. A bound particle that rotates in a magnetic field, which can be regarded as an out-off-plane rotation, changes its height above the binding surface and thereby puts its binding under stress.

It should be noted that the force applying unit 89 shown in FIG. 12 is a part of an analyzing device for cooperating with the binding device 1, i.e. the cartridge 1, for determining a substance within a fluid. Thus, the force applying unit 89 shown in FIG. 12 can be used instead of or in addition to the magnetic unit 23, 24 in the substance determining apparatus described above with reference to FIG. 4.

Although in the above described embodiments force has been applied to the particles bound to the binding surface by magnetic forces, in other embodiments, in addition or alternatively, the force applying unit can be adapted to apply another kind of force to the particles bound to the binding surface. For example, the force applying unit can be adapted to apply a fluidic force or an electrostatic force to the particles bound to the binding surface.

In an embodiment, the force applying unit is adapted to use electrostatic forces to push particles bound to the binding surface away from the binding surface for putting the bindings under stress. This can be performed by exchanging the fluidic buffer in a fluidic wash step, while the particles remain bound to the binding surface.

Both, the particles and the binding surface, have an electrostatic surface charge in the fluid due to absorption of ions from the fluid or dissociation of surface groups on the surfaces. Typically, in biosensor environments, the surface charge is negative for both, the particles and the binding surface, leading to a natural repulsion between particles and binding surface. Ions in the fluid can screen the charge of both surfaces, thereby decreasing the repulsion.

The layer over which screening takes place is called the double layer. The inverse double layer thickness $\kappa$, correlated to the Debye-Hueckel length $\lambda_D$ ($\lambda_D = \kappa^{-1}$), is given by:

$$\kappa = \sqrt{\frac{2000 e^2 N_A I_C}{\varepsilon_0 \varepsilon_r k_B T}}, \tag{12}$$

where e is the elementary charge, $N_A$ Avogadro's number, $I_C$ the ionic strength of the fluid, $\varepsilon_0$ the dielectric permittivity of free space, $\varepsilon_r$ the relative permittivity of the fluid and $k_B T$ the thermal energy.

The electrostatic interaction energy between a particle and a surface depends on the inverse double layer thickness and is given by:

$$E_{es} = ZR \cdot \exp(-\kappa h) \tag{13}$$

with R the particle radius, h the distance between the particle (bottom) and the surface and Z given by:

$$Z = 64\pi\varepsilon_0\varepsilon_r \left(\frac{k_B T}{e}\right)^2 \tanh\left(\frac{ze\psi_{particle}}{4k_B T}\right) \tanh\left(\frac{ze\psi_{surface}}{4k_B T}\right). \tag{14}$$

Here z is the electrolyte valence, and $\psi_{particle}$ and $\psi_{surface}$ the surface potentials of respectively the particle and the surface. The electrostatic force between a particle bound to the binding surface and the binding surface depends therefore on the ionic strength of the buffer and can be increased by decreasing the ion concentration in the fluid. Thus, by modifying the ion concentration in the fluid, stress applied to the bindings between the particles bound to the binding surface and the binding surface can be modified. The force applying unit can therefore be adapted such that the ion concentration in the fluid can be modified. The ion concentration can, for example, be changed by inserting a new fluid in the binding device such that the new fluid is present on the binding surface. For example, the analyzing device can be adapted to fill a new fluid into the binding device, which is preferentially a cartridge, along the same way which has been used for transferring the original fluid like the blood to the binding surface.

Generally, also the Van der Waals interaction is present between the particles bound to the binding surface and the binding surface. The Van der Waals interaction can be expressed by following equation:

$$E_{vdw} = -1/6 A_{132} \left[ \frac{R}{h} + \frac{R}{h+2R} + \ln\left(\frac{h}{h+2R}\right) \right] \quad (15)$$

with $A_{132}$ the Hamaker constant of a particle of material 1 on a surface of material 2 in a fluid of material 3. The value of the Hamaker constant is usually around a few $k_B T$, and can be positive (attractive) or slightly negative (repulsive, mainly due to the presence of proteins on the surfaces). The force between the particles bound to the binding surface and the binding surface is the negative gradient of the respective interaction term, i.e. e.g. the negative gradient of $E_{es}$ and $E_{vdw}$.

By varying the Hamaker constant, for example, by exchanging the fluid, the Van der Waals interaction between the bound particles and the binding surface and, thus, the stress applied to the bindings between the bound particles and the binding surface can be modified.

Referring again to FIG. 4, the substance determination apparatus 19 is comprised of the binding device 1 and the analyzing device 18. The binding device 1 is, in this embodiment, a cartridge including the particles and the binding surface and being adapted to receive the fluid 3. The analyzing device 18 can be regarded as a reader and includes the sensing unit 33, the particle release curve determination unit 42, the binding determination unit 40 and the substance determination unit 41. The binding device 1 is a disposable device and the analyzing device 18 is a re-useable device.

The analyzing device 18 further comprises an output unit 60 for outputting a value indicating the amount or concentration of the substance within the fluid. The output unit 60 is preferentially a display. The analyzing device 18 further comprises a control unit 61 for controlling the sensing unit 33, the particle release curve determination 42, the binding determination unit 40, the substance determination unit 41, and the output unit 60.

As already mentioned above, the binding device 1 is preferentially a cartridge for receiving a fluid like blood, saliva or urine, for filtering the fluid and for transferring the filtered fluid to the sensing site of the cartridge. The cartridge is disposable and is adapted for single use only. The analyzing device 18 is adapted to be used several times with different cartridges. Thus, a fluid 3 like blood, saliva or urine is put on the filter element 2 of the binding device 1, the fluid 3 is filtered and the filtered fluid is transferred to the sensing location 7. The binding device 1, i.e. in this embodiment the cartridge, is arranged in the analyzing device 18 and a substance within the fluid 3 at the sensing location is analyzed by the analyzing device 18. After the binding device 1 has been used, it is preferentially discarded, whereas the analyzing device 18 is used for a next analyzing procedure.

Figure 13:
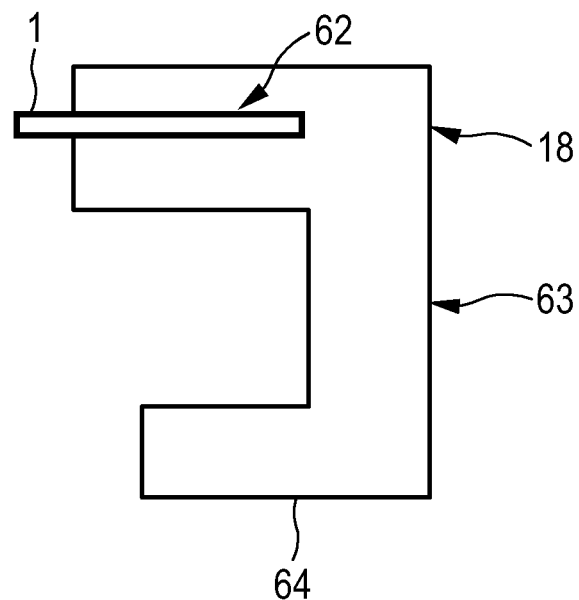
FIG. 13 shows schematically and exemplarily a binding device introduced into an analyzing device.

The several units of the analyzing device 18 are preferentially arranged within a casing 64, which is schematically and exemplarily shown in FIG. 13 and which can comprise a grip part 63 for allowing a user to hold the analyzing device 18 in the hand while analyzing the substance in the fluid. The casing 64 comprises a receiving section 62 for receiving the binding device 1. In other embodiments, the casing 64 can have another shape.

The several units of the analyzing device 18 can also be arranged within a casing not being a handheld casing. For example, the casing of the analyzing device can be adapted to stand on a table or the like.

Figure 14:
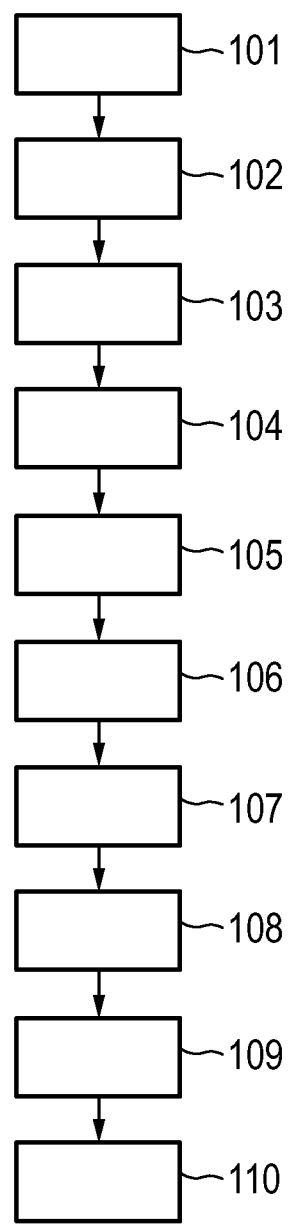
FIG. 14 shows a flowchart exemplarily illustrating a substance determining method for determining a substance in a fluid.

In the following a substance determining method for determining a substance within a fluid will exemplarily be described with reference to a flowchart shown in FIG. 14.

In step 101, a fluid sample, in particular, a blood sample, is arranged on the filter element 2.

In step 102, the fluid is filtered by the filter element 2, and in step 103 the filtered fluid is transferred to the sensing location 7 by capillary forces generated by the connecting channel and the guiding channels of the capillary structure.

Before, while or after performing steps 101 to 103 the binding device 1 has been introduced into the analyzing device 18. At the sensing location 7 magnetic particles coated with a specific antibody that attaches to a target molecule, i.e. the substance, present in the fluid are located. They mix with the filtered fluid, and the magnetic particles with the specific antibody attach to the target molecules within the fluid in step 104.

In step 105, the magnetic unit is controlled such that the magnetic particles at the sensing location 7 are forced onto the binding surface 30 in a binding phase. The magnetic particles with the attached target molecules bind to the binding surface 30 and in step 106, in a washing phase, the magnetic unit is controlled such that magnetic forces urge the magnetic particles away from the binding surface 30. This removes unbound particles from the binding surface and puts the bindings under stress. While the bindings are put under stress, a temporal sensing signal is generated depending on the bound particles. The temporal sensing signal is, for example, a FTIR signal generated by the first detector 21 or a DFM signal generated by the second detector 27. The DFM signal generated by the second detector 27 can also be used as both, a sensing signal and a position signal, or, if the FTIR signal generated by the first detector 21 is used as sensing signal, the DFM signal generated by the second detector 27 can only be used as position signal. The sensing signal and the position signal are preferentially generated as described above with reference to FIG. 4.

In step 107, a particle release curve being indicative of a release of bound particles from the binding surface is generated depending on the temporal sensing signal as described above as, for example, a FTIR signal or as a histogram of lifetimes of binding events, which can be determined based on the DFM signal. In another embodiment, lifetimes of binding events can also be determined in the binding phase, wherein a particle release curve can be determined as a histogram of the lifetimes of the binding events determined in the binding phase. In this case, in the binding phase the magnetic unit provides forces for urging the magnetic particles towards the binding surface and away from the binding surface, in order to allow the sensing unit to determine a sensing signal being indicative of starting moments and ending moments of binding events as described above.

In step 108, a part of the particle release curve caused by particles bound to the binding surface via a specific binding is determined based on the temporal behaviour of the particle release curve being preferentially the FTIR signal. In particular, a correction factor c(F) is determined depending on the force applied to the particles for putting the bindings under stress and the fitting function of equation (11) is fitted to the generated sensing signal for determining the fraction f, which is preferentially used in accordance with equation (10) for determining the part of the particle release curve caused by specifically bound particles. In an embodiment, also the positions of the particles can be determined by using the position signal being preferentially a DFM signal, wherein the determined positions are used for determining the particle-particle influence and wherein the correction factor is determined based on the applied force and the determined particle-particle interactions.

In step 109, the concentration and/or amount of the substance within the fluid is determined based on the determined part of the particle release curve. The substance determination unit can use assignments between determined parts of the particle release curve and concentrations and/or amounts of the substance within the fluid, wherein the assignments can be determined by calibration as described above in more detail.

In step 110, the determined substance, in particular, the determined amount and/or concentration of the substance, within the fluid is shown on the output unit 60.

Steps 101 to 105 can be regarded as the steps of a binding method, and steps 106 to 109 can be regarded as the steps of an analyzing method.

Although in the above described embodiments a linear combination of exponential decay curves having certain time constants being indicative of certain kinds of binding has been fitted to the particle release curve for determining a part of the particle release curve caused by particles bound to the binding surface via a predefined kind of binding, this part of the particle release curve can also be determined by using another fitting procedure. Generally, the binding determination unit can be adapted to provide a first predefined fitting release curve having a first temporal behaviour being indicative of a first kind of binding and a second predefined fitting release curve having a second temporal behaviour being indicative of a second kind of binding. The binding determination unit is preferentially further adapted to fit the first predefined fitting release curve and the second predefined fitting release curve to the determined particle release curve by fitting a linear combination of the first predefined fitting release curve and the second predefined fitting release curve to the determined particle release curve, wherein one of the fitted first predefined release curve and the fitted second predefined release curve is determined as the part of the particle release curve caused by particles bound to the binding surface via a predefined kind of binding. In an embodiment, the first predefined fitting release curve is a specific calibration curve having a specific temporal behaviour being indicative of a specific binding and the second predefined fitting release curve is a non-specific calibration curve having a non-specific temporal behaviour being indicative of a non-specific binding. A preferred fitting procedure can be described by following equation:

$$N(t)=f*g_{spec}(t)+(1-f)*g_{nonspec}(t). \quad (16)$$

In equation (16) $g_{spec}(t)$ indicates a specific calibration curve and $g_{nonspec}$ indicates a non-specific calibration curves. By performing the fitting procedure, the fraction f of specifically bound particles multiplied with the specific calibration curve can be regarded as the determined substance within the fluid, which has been determined based on the specific part of the particle release curve, or a concentration or an amount of the substance within the fluid can be determined based on the product of the fraction f and the specific calibration curve as the determined substance within the fluid.

The calibration curves can be defined either as real measured curves, for example, as a table with measured values, or as a parametric curve in which the parameters are determined by fitting the parametric curve to the measured curves. A parametric curve can be any model which describes the measured data such as a polynomial, a Fourier series, a linear superposition of exponentially decaying signals et cetera. In particular, a specific calibration curve can be determined, if only specifically bound particles are present, and a non-specific calibration curve can be determined, if only non-specifically bound particles are present.

In a further embodiment, a number of particle release curves is determined for known substance concentrations, wherein these measured particle release curves are regarded as concentration calibration curves. When determining a particle release curve with unknown concentration, the concentration can be determined from interpolation using the concentration calibration curves with known substance concentrations. As in the previous embodiment, the particle release curves of substances with known concentration can be parameterized using a certain mathematical function, yielding a set of parameter values at a certain concentration. Next, the release curve of the unknown substance is measured and parameterized using the same mathematical function, resulting in a set of parameters. Via interpolation of one or more of those parameters using the parameters of the parameterized concentration calibration curves, the unknown concentration can be determined.

The above mentioned calibration curves can be arbitrary mathematical models which do not have any relation with the real physical or chemical model. However, the mathematical models could also describe the reality in a more accurate way, as might be the case with linear superposition of exponential decaying functions. In this case also physical or chemical parameters like time constants or reaction constants can be extracted from the fitting. Such a fitting of a linear superposition of exponential decaying functions to the determined particle release curve is described above in more detail.

The substance determining apparatus is preferentially a magnetic biosensor that can be used to correct for non-specific binding. The substance determining apparatus is preferentially based on nanoparticles that can be actuated with electro-magnetic fields. The nanoparticles are preferentially magnetic beads which are functionalized with antibodies that can bind a specific analyte molecule. The beads are attracted to the binding surface, where the number of bound beads is directly or inversely related to the amount of analyte molecules present in the fluid sample. The beads are then preferentially detected by using a technique that is more sensitive to beads that are close to the binding surface than to beads that are more far away from the binding surface. The substance determining apparatus uses preferentially the above described FTIR technique and DFM technique. Using these techniques, the sensitivity to the nanoparticles decreases exponentially with an increasing distance from the surface. Generally, if the distance between the particles and the binding surface is larger, the corresponding sensing signal will be smaller. However, the sensing signal can also be defined such that a particle being close to the binding surface generates a smaller signal then a particle being more far away from the binding surface.

The binding device can be an optical cartridge being a carrier of a bioassay comprising particles being optical labels, preferably microscopic super-paramagnetic labels providing optical contrast by means of scattering and/or fluorescence.

Although in the above described embodiments total internal reflection has been used for inducing the evanescent field, in other embodiments other techniques can be used for inducing the evanescent field, for example, grating coupling or waveguide coupling can be used.

Although in the above mentioned embodiment described with reference to FIG. 4, a microscope objective 32 and an imaging lens 26 have been used, in other embodiments other optical elements for collecting and imaging of photons can be used. The objective lens is positioned at the bottom side of the binding device, underneath the horseshoe actuation magnet 23. The photons from the optical labels are transmitted through an air gap in between the two horseshoe magnets 23, before they are captured by the objective lens. The objective lens has a numerical aperture allowing imaging the individual optical labels onto the second light detector 27 being, for example, a CCD camera.

Although in a described embodiment the analyzing device is a handheld device, in other embodiments the analyzing device can also be a standalone system which is to be arranged on, for example, a table.

The substance determining apparatus can be adapted to determine the amount and/or concentration of particles which have been attached to certain substance, if several substances are present within the fluid, wherein particles which have been attached to these difference substances can bind to the binding surface, and wherein the bound particles which have been attached to different substances are distinguished by using the different temporal behaviours.

In the above described embodiment, the fluid was preferentially blood. In other embodiments, the fluid can be any other fluid, in particular, another body fluid, like saliva or urine. The preferred application for the binding device and for the analyzing device is in the field of point-of-care diagnostics, in particular, based on a finger prick blood sample, like a cardiac marker detection application. But, as mentioned above, the binding device can also be adapted for being used with other fluids like saliva for Drugs Of Abuse.

In the above described embodiments, the analyzing device apparatus uses evanescent field techniques for determining the amount of magnetic particles on the surface. In other embodiments, other techniques can be used for determining these particles. For example, magnetic methods, sonic detection, electrical detection and combinations therefore can be used. Furthermore, the analyzing device can comprise any sensor based on the detection of the magnetic properties of the particles on or near to a sensor surface. The analyzing device can be adapted for detecting molecular targets, which often determine the concentration and/or presence of larger moieties, for example, cells, viruses, fractions of cells or fractions of viruses, tissue extract et cetera. The magnetic particles can be detected directly by the sensing method. As well, the particles can be further processed prior to detection. An example of further processing is that materials are added or that the chemical, biochemical or physical properties of the magnetic labels are modified to facilitate detection. The analyzing device can be adapted for working together with several biochemical assay types, for example, binding/unbinding assay, sandwich assay, competition assay, displacement assay, enzymatic assay et cetera. The binding device and the analyzing device can be adapted for sensor multiplexing, i.e. the parallel use of different sensors and sensor surfaces, label multiplexing, i.e. the parallel use of different types of labels, and chamber multiplexing, i.e. the parallel use of different reaction chambers. The binding device and the analyzing device can be used as rapid, robust and easy to use point-of-care biosensors for small sample volumes. The sensing cavity is preferentially a part of a disposable cartridge, which is to be used with the analyzing device, which contains one or more magnetic field generating means, i.e. the magnetic unit, and one or more detection means. The binding device and the analyzing device can preferentially be adapted for use in automated high-throughput testing.

The particles are preferentially magnetic beads being preferentially nano-particles having at least one dimension ranging between 3 nm and 5000 nm, preferably between 10 nm and 3000 nm, more preferred between 50 nm and 1000 nm.

Although in the above described embodiments a certain binding device and a certain analyzing device have been described, in other embodiments the binding device and the analyzing device can have another structure. For example, the binding device can just comprise a binding surface. Or another kind of filter can be used or another channel structure can be used for transferring filtered fluid from a filter location to a sensing location.

Although in the above described embodiments the substance determining apparatus is comprised of a binding device and an analyzing device, in another embodiment the substance determining apparatus can be an integrated apparatus comprising at least the particles, the binding surface, the sensing unit, the binding determination unit and the substance determination unit.

The substance determining apparatus is preferentially adapted to determine the fraction of the generated sensing signal caused by specifically bound particles by a) using a physical force which enhances the desorption of the weakest bound particle to such a level that sensing signal changes are detectable within the time frame of the measurement, i.e. detectable within the sensing time, b) compensating for the time-dependence of the physical force by using the correction factor, and c) using a fitting method of the total particle release curve, to determine the fraction of the particle release curve caused by specifically bound particles. For compensation for the time-dependence of the physical force information about the in-plane and vertical positions of the particles obtained from the position signals can be used to estimate the time-dependent force on individual particles by means of numerical, real time calculations. The time-dependent force can be used for determining a time-dependent correction factor for correcting the time constants of the temporal behaviour of the particle release curve, thereby compensating for the time-dependence of the physical force.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Determinations like the determination of a particle release curve depending on a generated temporal sensing signal, of a part of the particle release curve caused by particles bound to the binding surface via a predefined kind of binding and of the substance within the fluid based on the determined part of the particle release curve performed by one or several units or devices can be performed by any other number of units or devices. For example, steps 106 to 109 can be performed by a single unit or by any other number of different units. The determinations and/or the control of the substance determining apparatus, in particular, of the analyzing device, in accordance with the analyzing method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a substance determining apparatus and method for determining a substance within a fluid. Particles attach to the substance and bind to a binding surface, wherein a particle release curve being indicative of a release of bound particles from the binding surface is determined, and a part of the particle release curve caused by particles bound to the binding surface via a predefined kind of binding is determined based on the temporal behaviour of the particle release curve. The substance within the fluid is determined based on the part of the particle release curve. The substance can therefore be determined based on particles which are bound to the binding surface via a certain kind of binding, i.e. other kinds of binding substantially do not affect the determination of the substance, thereby improving the accuracy of determining the substance.

The invention claimed is:

1. An apparatus for determining a substance within a fluid, the apparatus comprising:
    a cartridge having a channel including a sensing location having a sensing cavity and a binding surface for binding a plurality of particles having magnetic properties, wherein the binding surface is structured such that particles of the plurality of particles that bind to the binding surface bind with one of two types of binding with a first type of binding being a specific predetermined type of binding and a second type of binding being a non-specific type of binding;
    a particle detector configured to receive the cartridge and to generate a temporal position signal indicative of corresponding positions of the plurality of particles over a given temporal period;
    at least one light detector configured to receive and detect a reflection of radiation from a detection plane defined by the binding surface; and
    a processor and a processor storage medium having instructions stored thereon, the processor configured by the instructions stored on the processor storage medium to perform acts of
        determining a particle release curve indicative of a release of the bound particles from the binding surface based on the generated temporal position signal over the given temporal period,
        separating a part of the particle release curve caused by particles bound to the binding surface that are indicative of the first type of binding from the second type of binding based on a temporal behavior of the particle release curve over the given temporal period, and
        determining a substance within the fluid based only on the part of the particle release curve which is indicative of the first type of binding.

2. The apparatus as in claim 1, wherein the temporal position signal is dependent on the bound particles integrated over a predefined region of the binding surface, and the processor is further configured to determine the particle release curve from the generated temporal position signal over the given temporal period.

3. The apparatus as in claim 1, wherein the processor is further configured by the instructions stored on the processor storage medium to perform acts of:
    determining lifetimes of the bindings of the plurality of particles on the binding surface from the generated sensing signal,
    generating a histogram of the determined lifetimes, and
    determining the particle release curve depending on the generated histogram.

4. The apparatus as in claim 1, further comprising a stressing device for putting bindings between the particles and the binding surface under stress, while the particle detector senses the particles,
    wherein the cartridge comprises lower and upper substrates forming the channel and the stressing device comprises lower and upper magnets placed proximate the lower and upper substrates respectively, the lower and upper magnets are configured to apply a force to attract and repel the magnetic particles to and from the binding surface.

5. The apparatus as in claim 1, wherein the processor is further configured by the instructions stored on the processor storage medium to perform acts of:
    providing a plurality of predefined curves, each having a respective temporal behavior indicative of a respective type of binding between different particles bound to the binding surface; and
    determining a best fitting between linear combinations of the plurality of predefined curves and the determined particle release curve over the given temporal period.

6. The apparatus as in claim 1, wherein the processor is further configured by the instructions stored on the processor storage medium to perform acts of:
    determining the time constants of the particle release curve as the temporal behavior of the particle release curve, the time constants are defined by reaction constants of the plurality of particles bound to the binding surface over the given temporal period, and
    determining a part of the particle release curve which changes with at least one of the determined time constants based only on the part of the particle release curve caused by particles bound to the binding surface through the first type of binding.

7. The apparatus as in claim 6, further comprising a stressing device including a magnet for applying a force to the particles for putting bindings between the particles and the binding surface under stress, wherein the particle detector senses the particles under stress, and wherein the processor is further configured by the instructions stored on the processor storage medium to perform acts of
    correcting the time constants for the influence of the applied force based on the applied force, and
    determining a part of the particle release curve, which changes with at least one of the corrected time constants, as the part of the particle release curve caused by particles bound to the binding surface through the first type of binding.

8. The apparatus as in claim 6, wherein the processor is further is configured by the instructions stored on the processor storage medium to perform acts of:
    determining the positions of the particles for different times from the generated temporal position signal over the given temporal period,
    determining the magnetic particle-particle influence based on the determined positions and magnetic properties of the particles at the different times, correcting the time constants depending on the determined magnetic particle-particle influence at the different times, and determining a part of the particle release curve, which changes with at least one of the corrected time constants, as the part of the particle release curve caused by particles bound to the binding surface through the first type of binding.

9. The apparatus as in claim 8, wherein the sensor further comprises: a light source configured to generate and direct radiation to the binding surface for generating an evanescent field, wherein the temporal position signal is generated based on the detected reflection influenced by the evanescent field and is indicative of the positions of the plurality of particles within the detection plane over the given temporal period.

10. The apparatus as in claim 9, wherein the light detector is configured to move the detection plane with respect to the binding surface for generating the temporal position signal indicative of height positions of the particles with respect to the binding surface.

11. A method for determining a substance within a fluid on a cartridge, the method comprising acts of:

attaching a portion of a plurality of particles having magnetic properties to the substance within the fluid;

structuring a binding surface of the cartridge such that particles of the plurality of particles that bind to the binding surface bind with one of two types of binding with a first type of binding being a specific predetermined type of binding and a second type of binding being a non-specific type of binding;

binding the plurality of particles to the binding surface of the cartridge;

generating a temporal position signal indicative of corresponding positions of the plurality of particles;

receiving and detecting a reflection of radiation from a detection plane defined by the binding surface;

determining a particle release curve indicative of a release of the bound particles from the binding surface using the generated temporal position signal over a given temporal period;

separating a part of the particle release curve caused by particles bound to the binding surface that are indicative of the first type of binding from the second type of binding based on a temporal behavior of the particle release curve over the given temporal period; and determining the substance within the fluid based only on the part of the particle release curve which is indicative of the first type of binding.

12. An analyzing method for determining a substance within a fluid, the analyzing method comprising:

generating a temporal position signal indicative of corresponding positions of a portion of a plurality of particles having magnetic properties being attached to the substance within the fluid and bound on a binding surface of a cartridge including the fluid, wherein the binding surface is structured such that particles of the plurality of particles bound to the binding surface bind with one of two types of binding with a first type of binding being a specific predetermined type of binding and a second type of binding being a non-specific type of binding;

receiving and detecting a reflection of radiation from a detection plane defined by the binding surface;

determining a particle release curve indicative of the release of the bound particles from the binding surface based on the generated temporal position signal over a given temporal period;

separating a part of the particle release curve caused by particles bound to the binding surface that are indicative of the first type of binding from the second type of binding based on a temporal behavior of the particle release curve over the given temporal period; and determining the substance within the fluid based only on the part of the particle release curve which is indicative of the first type of binding.

13. The apparatus as in claim 1, wherein the cartridge comprises:

proximal and distal ends;

a lower substrate having a capillary structure at the proximal end;

an upper substrate attached to the lower substrate and including a vent at the distal end, the upper and lower substrates are transparent to visible light;

a filter attached to the lower substrate at the proximal end over a filtering location;

the channel having a sensing cavity including the binding surface, the channel is formed between the lower substrate and the upper substrate connecting the capillary structure and the vent.

* * * * *